(12) United States Patent
Wicks et al.

(10) Patent No.: US 8,968,731 B2
(45) Date of Patent: Mar. 3, 2015

(54) TREATMENT OF UVEITIS

(75) Inventors: Ian Peter Wicks, Kew (AU); Ian Keith Campbell, Wantirna South (AU); Ann Leckie Cornish, Camberwell (AU)

(73) Assignee: CSL Limited, Parkville, Victoria (AU)

( * ) Notice: Subject to any disclaimer, the term of this patent is extended or adjusted under 35 U.S.C. 154(b) by 371 days.

(21) Appl. No.: 12/900,688

(22) Filed: Oct. 8, 2010

(65) Prior Publication Data

US 2011/0110934 A1     May 12, 2011

Related U.S. Application Data

(60) Provisional application No. 61/250,101, filed on Oct. 9, 2009.

(51) Int. Cl.
| | |
|---|---|
| A61K 39/395 | (2006.01) |
| A61K 39/00 | (2006.01) |
| C07K 16/24 | (2006.01) |
| A61K 31/7088 | (2006.01) |
| A61K 45/06 | (2006.01) |
| C07K 16/28 | (2006.01) |
| A61K 38/17 | (2006.01) |

(52) U.S. Cl.
CPC ........... *C07K 16/243* (2013.01); *A61K 31/7088* (2013.01); *A61K 39/395* (2013.01); *A61K 45/06* (2013.01); *C07K 16/2866* (2013.01); *A61K 38/1793* (2013.01); *A61K 2039/505* (2013.01); *C07K 2317/73* (2013.01); *C07K 2317/76* (2013.01)
USPC .................. 424/130.1; 424/133.1; 424/141.1; 424/143.1; 424/145.1; 424/158.1

(58) Field of Classification Search
None
See application file for complete search history.

(56) References Cited

U.S. PATENT DOCUMENTS

| 5,961,977 A * | 10/1999 | Hafler et al. ............... 424/184.1 |
| 6,861,056 B2 * | 3/2005 | Skurkovich et al. ....... 424/134.1 |
| 7,108,852 B2 * | 9/2006 | Devalaraja et al. ........ 424/130.1 |

OTHER PUBLICATIONS

Tsuchiyama et al. 2000. Ann Hematol. 79: 269-271.*
Reiff et al. 2001. Arthritis and Rheumatism. 44:1411-1415.*
Suarenmann et al. 2006. Rheumatology. 45:982-989.*
Kruithof et al. 2002. Ann Rheum Dis. 61:470.*
Brendolan, A. et al., "Treatment of adjuvant arthritis with granulocyte-colony stimulating factor and peptide derived from heat shock protein 65", Cellular Immunology, 221:6-14 (2003).
Franzke, A., et al., "G-CSF as immune regulator in T cells expressing the G-CSF receptor: implications for transplantation and autoimmune diseases", Blood, 102(2):734-739 (2002).
Lock, C., et al., "Gene-microarray analysis of multiple sclerosis lesions yields new targets validated in autoimmune encephalomyelitis", Nature Medicine, 8(5):500-508 (2002).
Zavala, F., et al., "G-CSF Therapy of Ongoing Experimental Allergic Encephalomyelitis Via Chemokine- and Cytokine-Based Immune Deviation", The Journal of Immunology, 168:2011-2019 (2002).

* cited by examiner

*Primary Examiner* — Shulamith H Shafer
(74) *Attorney, Agent, or Firm* — Scully, Scott, Murphy & Presser P.C.

(57) ABSTRACT

The present invention relates generally to the use of antagonists of G-CSF, and/or its receptor (G-CSFR) in the treatment of uveitis. The present invention contemplates, therefore, the inhibition of G-CSF or G-CSFR systemically or locally and/or the down-regulation of expression of a G-CSF or G-CSFR in the treatment of uveitis.

8 Claims, 3 Drawing Sheets

SEQUENCE LISTING

<160> NUMBER OF SEQ ID NOS: 8

<210> SEQ ID NO 1
<211> LENGTH: 204
<212> TYPE: PRT
<213> ORGANISM: Homo sapiens

<400> SEQUENCE: 1

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
        195                 200

<210> SEQ ID NO 2
<211> LENGTH: 1498
<212> TYPE: DNA
<213> ORGANISM: Homo sapiens

<400> SEQUENCE: 2
ggagcctgca gcccagcccc acccagaccc atggctggac ctgccaccca gagccccatg      60
aagctgatgg ccctgcagct gctgctgtgg cacagtgcac tctggacagt gcaggaagcc    120 accccctgg gccctgccag ctccctgccc cagagcttcc tgctcaagtg cttagagcaa     180
gtgaggaaga tccagggcga tggcgcagcg ctccaggaga agctgtgtgc cacctacaag    240
ctgtgccacc ccgaggagct ggtgctgctc ggacactctc tgggcatccc ctgggctccc    300
ctgagcagct gccccagcca ggccctgcag ctggcaggct gcttgagcca actccatagc    360
ggccttttcc tctaccaggg gctcctgcag gccctggaag gatctccccc gagttgggt    420 cccaccttgg acacactgca gctggacgtc gccgactttg ccaccaccat ctggcagcag    480
atggaagaac tgggaatggc ccctgccctg cagcccaccc agggtgccat gccggccttc    540
gcctctgctt tccagcgccg gcaggagggg tcctagttg cctcccatct gcagagcttc     600
ctggaggtgt cgtaccgcgt tctacgccac cttgcccagc cctgagccaa gcctccccca    660

```
tcccatgtat ttatctctat ttaatattta tgtctattta agcctcatat ttaaagacag     720
ggaagagcag aacggagccc caggcctctg tgtccttccc tgcatttctg agtttcattc     780
tcctgcctgt agcagtgaga aaaagctcct gtcctcccat cccctggact gggaggtaga     840
taggtaaata ccaagtattt attactatga ctgctcccca gccctggctc tgcaatgggc     900
actgggatga gccgctgtga gcccctggtc ctgagggtcc ccacctggga cccttgagag     960
tatcaggtct cccacgtggg agacaagaaa tccctgttta atatttaaac agcagtgttc    1020
cccatctggg tccttgcacc cctcactctg gcctcagccg actgcacagc ggcccctgca    1080
tccccttggc tgtgaggccc ctggacaagc agaggtggcc agagctggga ggcatggccc    1140
tggggtccca cgaatttgct ggggaatctc gttttcttc ttaagacttt tgggacatgg     1200
tttgactccc gaacatcacc gacgcgtctc ctgtttttct gggtggcctc gggacacctg    1260
ccctgccccc acgagggtca ggactgtgac tcttttagg gccaggcagg tgcctggaca    1320
tttgccttgc tggacgggga ctggggatgt gggagggagc agacaggagg aatcatgtca    1380
ggcctgtgtg tgaaaggaag ctccactgtc accctccacc tcttcaccc ccactcacca    1440 gtgtcccctc cactgtcaca ttgtaactga acttcaggat aataaagtgc ttgcctcc     1498

<210> SEQ ID NO 3
<211> LENGTH: 525
<212> TYPE: DNA
<213> ORGANISM: Homo sapiens

<400> SEQUENCE: 3
acccccctgg gccctgccag ctccctgccc cagagcttcc tgctcaagtg cttagagcaa      60
gtgaggaaga tccagggcga tggcgcagcg ctccaggaga agctgtgtgc cacctacaag     120
ctgtgccacc ccgaggagct ggtgctgctc ggacactctc tgggcatccc ctgggctccc     180
ctgagcagct gccccagcca ggccctgcag ctggcaggct gcttgagcca actccatagc     240
ggccttttcc tctaccaggg gctcctgcag gccctggaag gatctccccc cgagttgggt     300
cccaccttgg acacactgca gctggacgtc gccgactttg ccaccaccat ctggcagcag     360
atggaagaac tgggaatggc ccctgccctg cagcccaccc agggtgccat gccggccttc     420
gcctctgctt tccagcgccg gcaggaggg gtcctagttg cctcccatct gcagagcttc     480
ctggaggtgt cgtaccgcgt tctacgccac cttgcccagc cctga                     525

<210> SEQ ID NO 4
<211> LENGTH: 174
<212> TYPE: PRT
<213> ORGANISM: Homo sapiens

<400> SEQUENCE: 4

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95
```

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
            130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 5
<211> LENGTH: 863
<212> TYPE: PRT
<213> ORGANISM: Homo sapiens

<400> SEQUENCE: 5

Met Ala Arg Leu Gly Asn Cys Ser Leu Thr Trp Ala Ala Leu Ile Ile
1               5                   10                  15

Leu Leu Leu Pro Gly Ser Leu Glu Glu Cys Gly His Ile Ser Val Ser
            20                  25                  30

Ala Pro Ile Val His Leu Gly Asp Pro Ile Thr Ala Ser Cys Ile Ile
            35                  40                  45

Lys Gln Asn Cys Ser His Leu Asp Pro Glu Pro Gln Ile Leu Trp Arg
        50                  55                  60

Leu Gly Ala Glu Leu Gln Pro Gly Gly Arg Gln Gln Arg Leu Ser Asp
65                  70                  75                  80

Gly Thr Gln Glu Ser Ile Ile Thr Leu Pro His Leu Asn His Thr Gln
                85                  90                  95

Ala Phe Leu Ser Cys Cys Leu Asn Trp Gly Asn Ser Leu Gln Ile Leu
            100                 105                 110

Asp Gln Val Glu Leu Arg Ala Gly Tyr Pro Pro Ala Ile Pro His Asn
            115                 120                 125

Leu Ser Cys Leu Met Asn Leu Thr Thr Ser Ser Leu Ile Cys Gln Trp
            130                 135                 140

Glu Pro Gly Pro Glu Thr His Leu Pro Thr Ser Phe Thr Leu Lys Ser
145                 150                 155                 160

Phe Lys Ser Arg Gly Asn Cys Gln Thr Gln Gly Asp Ser Ile Leu Asp
                165                 170                 175

Cys Val Pro Lys Asp Gly Gln Ser His Cys Cys Ile Pro Arg Lys His
            180                 185                 190

Leu Leu Leu Tyr Gln Asn Met Gly Ile Trp Val Gln Ala Glu Asn Ala
            195                 200                 205

Leu Gly Thr Ser Met Ser Pro Gln Leu Cys Leu Asp Pro Met Asp Val
            210                 215                 220

Val Lys Leu Glu Pro Pro Met Leu Arg Thr Met Asp Pro Ser Pro Glu
225                 230                 235                 240

Ala Ala Pro Pro Gln Ala Gly Cys Leu Gln Leu Cys Trp Glu Pro Trp
                245                 250                 255

Gln Pro Gly Leu His Ile Asn Gln Lys Cys Glu Leu Arg His Lys Pro
            260                 265                 270

Gln Arg Gly Glu Ala Ser Trp Ala Leu Val Gly Pro Leu Pro Leu Glu
            275                 280                 285

Ala Leu Gln Tyr Glu Leu Cys Gly Leu Leu Pro Ala Thr Ala Tyr Thr

-continued

```
                290                 295                 300
Leu Gln Ile Arg Cys Ile Arg Trp Pro Leu Pro Gly His Trp Ser Asp
305                 310                 315                 320

Trp Ser Pro Ser Leu Glu Leu Arg Thr Thr Glu Arg Ala Pro Thr Val
                325                 330                 335

Arg Leu Asp Thr Trp Trp Arg Gln Arg Gln Leu Asp Pro Arg Thr Val
                340                 345                 350

Gln Leu Phe Trp Lys Pro Val Pro Leu Glu Glu Asp Ser Gly Arg Ile
                355                 360                 365

Gln Gly Tyr Val Val Ser Trp Arg Pro Ser Gly Gln Ala Gly Ala Ile
                370                 375                 380

Leu Pro Leu Cys Asn Thr Thr Glu Leu Ser Cys Thr Phe His Leu Pro
385                 390                 395                 400

Ser Glu Ala Gln Glu Val Ala Leu Val Ala Tyr Asn Ser Ala Gly Thr
                405                 410                 415

Ser Arg Pro Thr Pro Val Val Phe Ser Glu Ser Arg Gly Pro Ala Leu
                420                 425                 430

Thr Arg Leu His Ala Met Ala Arg Asp Pro His Ser Leu Trp Val Gly
                435                 440                 445

Trp Glu Pro Pro Asn Pro Trp Pro Gln Gly Tyr Val Ile Glu Trp Gly
                450                 455                 460

Leu Gly Pro Pro Ser Ala Ser Asn Ser Asn Lys Thr Trp Arg Met Glu
465                 470                 475                 480

Gln Asn Gly Arg Ala Thr Gly Phe Leu Leu Lys Glu Asn Ile Arg Pro
                485                 490                 495

Phe Gln Leu Tyr Glu Ile Ile Val Thr Pro Leu Tyr Gln Asp Thr Met
                500                 505                 510

Gly Pro Ser Gln His Val Tyr Ala Tyr Ser Gln Glu Met Ala Pro Ser
                515                 520                 525

His Ala Pro Glu Leu His Leu Lys His Ile Gly Lys Thr Trp Ala Gln
                530                 535                 540

Leu Glu Trp Val Pro Glu Pro Pro Glu Leu Gly Lys Ser Pro Leu Thr
545                 550                 555                 560

His Tyr Thr Ile Phe Trp Thr Asn Ala Gln Asn Gln Ser Phe Ser Ala
                565                 570                 575

Ile Leu Asn Ala Ser Ser Arg Gly Phe Val Leu His Gly Leu Glu Pro
                580                 585                 590

Ala Ser Leu Tyr His Ile His Leu Met Ala Ala Ser Gln Ala Gly Ala
                595                 600                 605

Thr Asn Ser Thr Val Leu Thr Leu Met Thr Leu Thr Pro Glu Gly Ser
                610                 615                 620

Glu Leu His Ile Ile Leu Gly Leu Phe Gly Leu Leu Leu Leu Leu Thr
625                 630                 635                 640

Cys Leu Cys Gly Thr Ala Trp Leu Cys Cys Ser Pro Asn Arg Lys Asn
                645                 650                 655

Pro Leu Trp Pro Ser Val Pro Asp Pro Ala His Ser Ser Leu Gly Ser
                660                 665                 670

Trp Val Pro Thr Ile Met Glu Glu Leu Pro Gly Pro Arg Gln Gly Gln
                675                 680                 685

Trp Leu Gly Gln Thr Ser Glu Met Ser Arg Ala Leu Thr Pro His Pro
                690                 695                 700

Cys Val Gln Asp Ala Phe Gln Leu Pro Gly Leu Gly Thr Pro Pro Ile
705                 710                 715                 720
```

```
Thr Lys Leu Thr Val Leu Glu Glu Asp Glu Lys Lys Pro Val Pro Trp
            725                 730                 735
Glu Ser His Asn Ser Ser Glu Thr Cys Gly Leu Pro Thr Leu Val Gln
        740                 745                 750
Thr Tyr Val Leu Gln Gly Asp Pro Arg Ala Val Ser Thr Gln Pro Gln
    755                 760                 765
Ser Gln Ser Gly Thr Ser Asp Gln Val Leu Tyr Gly Gln Leu Leu Gly
770                 775                 780
Ser Pro Thr Ser Pro Gly Pro Gly His Tyr Leu Arg Cys Asp Ser Thr
785                 790                 795                 800
Gln Pro Leu Leu Ala Gly Leu Thr Pro Ser Pro Lys Ser Tyr Glu Asn
                805                 810                 815
Leu Trp Phe Gln Ala Ser Pro Leu Gly Thr Leu Val Thr Pro Ala Pro
            820                 825                 830
Ser Gln Glu Asp Asp Cys Val Phe Gly Pro Leu Leu Asn Phe Pro Leu
        835                 840                 845
Leu Gln Gly Ile Arg Val His Gly Met Glu Ala Leu Gly Ser Phe
    850                 855                 860

<210> SEQ ID NO 6
<211> LENGTH: 3024
<212> TYPE: DNA
<213> ORGANISM: Homo sapiens

<400> SEQUENCE: 6
gaagctggac tgcagctggt ttcaggaact tctcttgacg agaagagaga ccaaggaggc      60
caagcagggg ctgggccaga ggtgccaaca tggggaaact gaggctcggc tcggaaaggt     120
gaagtaactt gtccaagatc acaaagctgg tgaacatcaa gttggtgcta tgcaaggct      180 gggaaactgc agcctgactt gggctgccct gatcatcctg ctgctccccg aagtctgga     240 ggagtgcggg cacatcagtg tctcagcccc catcgtccac ctgggggatc ccatcacagc     300
ctcctgcatc atcaagcaga actgcagcca tctggacccg agccacagat tctgtggag      360 actgggagca gagcttcagc ccgggggcag gcagcagcgt ctgtctgatg ggacccagga     420
atctatcatc accctgcccc acctcaacca cactcaggcc tttctctcct gctgcctgaa     480
ctggggcaac agcctgcaga tcctggacca ggttgagctg cgcgcaggct accctccagc     540 catacccca acctctcct gcctcatgaa cctcacaacc agcagcctca tctgccagtg       600
ggagccagga cctgagaccc acctaccac cagcttcact ctgaagagtt tcaagagccg      660
gggcaactgt cagacccaag gggactccat cctggactgc gtgcccaagg acgggcagag     720
ccactgctgc atcccacgca aacacctgct gttgtaccag aatatgggca tctgggtgca     780
ggcagagaat gcgctgggga ccagcatgtc cccacaactg tgtcttgatc ccatggatgt     840
tgtgaaactg gagcccccca tgctgcggac catggacccc agccctgaag cggcccctcc     900
ccaggcaggc tgcctacagc tgtgctggga gccatggcag ccaggcctgc acataaatca     960
gaagtgtgag ctgcgccaca gccgcagcg tggagaagcc agctgggcac tggtgggccc    1020 cctcccttg gaggccctc agtatgagct ctgcgggctc ctcccagcca cggcctacac     1080
cctgcagata cgctgcatcc gctggcccct gcctggccac tggagcgact ggagccccag    1140
cctggagctg agaactaccg aacgggcccc cactgtcaga ctggacacat ggtggcggca    1200
gaggcagctg accccagga cagtgcagct gttctggaag ccagtgcccc tggaggaaga    1260
cagcggacgg atccaaggtt atgtggtttc ttggagaccc tcaggccagg ctgggcat     1320
```

```
cctgcccctc tgcaacacca cagagctcag ctgcaccttc cacctgcctt cagaagccca   1380
ggaggtggcc cttgtggcct ataactcagc cgggacctct cgccccaccc cggtggtctt   1440
ctcagaaagc agaggcccag ctctgaccag actccatgcc atggcccgag accctcacag   1500
cctctgggta ggctgggagc cccccaatcc atggcctcag ggctatgtga ttgagtgggg   1560
cctgggcccc cccagcgcga gcaatagcaa caagacctgg aggatggaac agaatgggag   1620
agccacgggg tttctgctga aggagaacat caggcccttt cagctctatg agatcatcgt   1680
gactcccttg taccaggaca ccatgggacc ctcccagcat gtctatgcct actctcaaga   1740
aatggctccc tcccatgccc cagagctgca tctaaagcac attggcaaga cctgggcaca   1800
gctggagtgg gtgcctgagc ccctgagct ggggaagagc ccccttaccc actacaccat    1860
cttctggacc aacgctcaga accagtcctt ctccgccatc ctgaatgcct cctcccgtgg   1920
ctttgtcctc catggcctgg agcccgccag tctgtatcac atccacctca tggctgccag   1980
ccaggctggg gccaccaaca gtacagtcct caccctgatg accttgaccc cagagggggtc  2040 ggagctacac atcatcctgg gcctgttcgg cctcctgctg ttgctcacct gcctctgtgg   2100
aactgcctgg ctctgttgca gccccaacag gaagaatccc ctctggccaa gtgtcccaga   2160
cccagctcac agcagcctgg gctcctgggt gcccacaatc atggaggagc tgcccggacc   2220
cagacaggga cagtggctgg ggcagacatc tgaaatgagc cgtgctctca ccccacatcc   2280
ttgtgtgcag gatgccttcc agctgcccgg ccttggcacg ccacccatca ccaagctcac   2340
agtgctggag gaggatgaaa agaagccggt gccctgggag tcccataaca gctcagagac   2400
ctgtggcctc cccactctgg tccagaccta tgtgctccag ggggacccaa gagcagtttc   2460
cacccagccc caatcccagt ctggcaccag cgatcaggtc ctttatgggc agctgctggg   2520 cagcccccaca agcccagggc cagggcacta tctccgctgt gactccactc agcccctctt   2580
ggcgggcctc accccagcc ccaagtccta tgagaacctc tggttccagg ccagccccttt   2640 ggggaccctg gtaaccccag ccccaagcca ggaggacgac tgtgtctttg ggccactgct   2700
caacttcccc ctcctgcagg ggatccgggt ccatgggatg gaggcgctgg ggagcttcta   2760
gggcttcctg gggttcccctt cttgggcctg cctcttaaag gcctgagcta gctggagaag   2820 agggagggt ccataagccc atgactaaaa actaccccag cccaggctct caccatctcc    2880
agtcaccagc atccctct cctcccaatc tccataggct gggcctccca ggcgatctgc     2940
atactttaag gaccagatca tgctccatcc agccccaccc aatggccttt tgtgcttgtt   3000
tcctataact tcagtattgt aaac                                         3024
```

<210> SEQ ID NO 7
<211> LENGTH: 2520
<212> TYPE: DNA
<213> ORGANISM: Homo sapiens

<400> SEQUENCE: 7

```
gagtgcgggc acatcagtgt ctcagccccc atcgtccacc tgggggatcc catcacagcc     60
tcctgcatca tcaagcagaa ctgcagccat ctggacccgg agccacagat tctgtggaga    120
ctgggagcag agcttcagcc cggggggcagg cagcagcgtc tgtctgatgg gacccaggaa   180
tctatcatca ccctgcccca cctcaaccac actcaggcct ttctctcctg ctgcctgaac    240
tggggcaaca gcctgcagat cctggaccag gttgagctgc gcgcaggcta ccctccagcc   300
ataccccaca acctctcctg cctcatgaac ctcacaacca gcagcctcat ctgccagtgg   360
```

| | |
|---|---|
| gagccaggac ctgagaccca cctacccacc agcttcactc tgaagagttt caagagccgg | 420 |
| ggcaactgtc agacccaagg ggactccatc ctggactgcg tgcccaagga cgggcagagc | 480 |
| cactgctgca tcccacgcaa acacctgctg ttgtaccaga atatgggcat ctgggtgcag | 540 |
| gcagagaatg cgctggggac cagcatgtcc ccacaactgt gtcttgatcc catggatgtt | 600 |
| gtgaaactgg agcccccat gctgcggacc atggacccca gccctgaagc ggcccctccc | 660 |
| caggcaggct gcctacagct gtgctgggag ccatggcagc caggcctgca cataaatcag | 720 |
| aagtgtgagc tgcgccacaa gccgcagcgt ggagaagcca gctgggcact ggtgggcccc | 780 |
| ctccccttgg aggcccttca gtatgagctc tgcgggctcc tcccagccac ggcctacacc | 840 |
| ctgcagatac gctgcatccg ctggcccctg cctggccact ggagcgactg gagccccagc | 900 |
| ctggagctga gaactaccga acgggccccc actgtcagac tggacacatg gtggcggcag | 960 |
| aggcagctgg accccaggac agtgcagctg ttctggaagc cagtgccct ggaggaagac | 1020 |
| agcggacgga tccaaggtta tgtggtttct tggagaccct caggccaggc tggggccatc | 1080 |
| ctgccccctct gcaacaccac agagctcagc tgcaccttcc acctgccttc agaagcccag | 1140 |
| gaggtggccc ttgtggccta taactcagcc gggacctctc gccccacccc ggtggtcttc | 1200 |
| tcagaaagca gaggcccagc tctgaccaga ctccatgcca tggcccgaga ccctcacagc | 1260 |
| ctctgggtag ctgggagcc ccccaatcca tggcctcagg gctatgtgat tgagtggggc | 1320 |
| ctgggccccc ccagcgcgag caatagcaac aagacctgga ggatgaaaca gaatgggaga | 1380 |
| gccacggggt ttctgctgaa ggagaacatc aggccctttc agctctatga gatcatcgtg | 1440 |
| actcccttgt accaggacac catgggaccc tcccagcatg tctatgccta ctctcaagaa | 1500 |
| atggctccct cccatgcccc agagctgcat ctaaagcaca ttggcaagac ctgggcacag | 1560 |
| ctggagtggg tgcctgagcc ccctgagctg ggaagagcc cccttaccca ctacaccatc | 1620 |
| ttctggacca acgctcagaa ccagtccttc tccgccatcc tgaatgcctc ctcccgtggc | 1680 |
| tttgtcctcc atggcctgga gcccgccagt ctgtatcaca tccacctcat ggctgccagc | 1740 |
| caggctgggg ccaccaacag tacagtcctc accctgatga ccttgacccc agaggggtcg | 1800 |
| gagctacaca tcatcctggg cctgttcggc ctcctgctgt tgctcacctg cctctgtgga | 1860 |
| actgcctggc tctgttgcag ccccaacagg aagaatcccc tctggccaag tgtcccagac | 1920 |
| ccagctcaca gcagcctggg ctcctgggtg cccacaatca tggaggagct gcccggaccc | 1980 |
| agacagggac agtggctggg gcagacatct gaaatgagcc gtgctctcac cccacatcct | 2040 |
| tgtgtgcagg atgccttcca gctgccggc cttggcacgc cacccatcac caagctcaca | 2100 |
| gtgctggagg aggatgaaaa gaagccggtg ccctgggagt cccataacag ctcagagacc | 2160 |
| tgtggcctcc ccactctggt ccagacctat gtgctccagg ggacccaag agcagtttcc | 2220 |
| acccagcccc aatcccagtc tggcaccagc gatcaggtcc tttatgggca gctgctgggc | 2280 |
| agccccacaa gccagggcc agggcactat ctccgctgtg actccactca gccctcttg | 2340 |
| gcgggcctca ccccccagccc caagtcctat gagaacctct ggttccaggc cagccccttg | 2400 |
| gggaccctgg taaccccagc cccaagccag gaggacgact gtgtctttgg gccactgctc | 2460 |
| aacttccccc tcctgcaggg gatccgggtc catgggatgg aggcgctggg gagcttctag | 2520 |

<210> SEQ ID NO 8
<211> LENGTH: 839
<212> TYPE: PRT
<213> ORGANISM: Homo sapiens

<400> SEQUENCE: 8

```
Glu Cys Gly His Ile Ser Val Ser Ala Pro Ile Val His Leu Gly Asp
1               5                   10                  15

Pro Ile Thr Ala Ser Cys Ile Ile Lys Gln Asn Cys Ser His Leu Asp
                20                  25                  30

Pro Glu Pro Gln Ile Leu Trp Arg Leu Gly Ala Glu Leu Gln Pro Gly
            35                  40                  45

Gly Arg Gln Gln Arg Leu Ser Asp Gly Thr Gln Glu Ser Ile Ile Thr
50                  55                  60

Leu Pro His Leu Asn His Thr Gln Ala Phe Leu Ser Cys Cys Leu Asn
65                  70                  75                  80

Trp Gly Asn Ser Leu Gln Ile Leu Asp Gln Val Glu Leu Arg Ala Gly
                85                  90                  95

Tyr Pro Pro Ala Ile Pro His Asn Leu Ser Cys Leu Met Asn Leu Thr
                100                 105                 110

Thr Ser Ser Leu Ile Cys Gln Trp Glu Pro Gly Pro Glu Thr His Leu
            115                 120                 125

Pro Thr Ser Phe Thr Leu Lys Ser Phe Lys Ser Arg Gly Asn Cys Gln
        130                 135                 140

Thr Gln Gly Asp Ser Ile Leu Asp Cys Val Pro Lys Asp Gly Gln Ser
145                 150                 155                 160

His Cys Cys Ile Pro Arg Lys His Leu Leu Leu Tyr Gln Asn Met Gly
                165                 170                 175

Ile Trp Val Gln Ala Glu Asn Ala Leu Gly Thr Ser Met Ser Pro Gln
                180                 185                 190

Leu Cys Leu Asp Pro Met Asp Val Val Lys Leu Glu Pro Pro Met Leu
            195                 200                 205

Arg Thr Met Asp Pro Ser Pro Glu Ala Pro Pro Gln Ala Gly Cys
210                 215                 220

Leu Gln Leu Cys Trp Glu Pro Trp Gln Pro Gly Leu His Ile Asn Gln
225                 230                 235                 240

Lys Cys Glu Leu Arg His Lys Pro Gln Arg Gly Glu Ala Ser Trp Ala
                245                 250                 255

Leu Val Gly Pro Leu Pro Leu Glu Ala Leu Gln Tyr Glu Leu Cys Gly
            260                 265                 270

Leu Leu Pro Ala Thr Ala Tyr Thr Leu Gln Ile Arg Cys Ile Arg Trp
        275                 280                 285

Pro Leu Pro Gly His Trp Ser Asp Trp Ser Pro Ser Leu Glu Leu Arg
        290                 295                 300

Thr Thr Glu Arg Ala Pro Thr Val Arg Leu Asp Thr Trp Trp Arg Gln
305                 310                 315                 320

Arg Gln Leu Asp Pro Arg Thr Val Gln Leu Phe Trp Lys Pro Val Pro
                325                 330                 335

Leu Glu Glu Asp Ser Gly Arg Ile Gln Gly Tyr Val Val Ser Trp Arg
            340                 345                 350

Pro Ser Gly Gln Ala Gly Ala Ile Leu Pro Leu Cys Asn Thr Thr Glu
        355                 360                 365

Leu Ser Cys Thr Phe His Leu Pro Ser Glu Ala Gln Glu Val Ala Leu
    370                 375                 380

Val Ala Tyr Asn Ser Ala Gly Thr Ser Arg Pro Thr Pro Val Val Phe
385                 390                 395                 400

Ser Glu Ser Arg Gly Pro Ala Leu Thr Arg Leu His Ala Met Ala Arg
                405                 410                 415
```

```
Asp Pro His Ser Leu Trp Val Gly Trp Glu Pro Asn Pro Trp Pro
            420                 425                 430

Gln Gly Tyr Val Ile Glu Trp Gly Leu Gly Pro Pro Ser Ala Ser Asn
                435                 440                 445

Ser Asn Lys Thr Trp Arg Met Glu Gln Asn Gly Arg Ala Thr Gly Phe
            450                 455                 460

Leu Leu Lys Glu Asn Ile Arg Pro Phe Gln Leu Tyr Glu Ile Ile Val
465                 470                 475                 480

Thr Pro Leu Tyr Gln Asp Thr Met Gly Pro Ser Gln His Val Tyr Ala
                485                 490                 495

Tyr Ser Gln Glu Met Ala Pro Ser His Ala Pro Glu Leu His Leu Lys
            500                 505                 510

His Ile Gly Lys Thr Trp Ala Gln Leu Glu Trp Val Pro Glu Pro Pro
            515                 520                 525

Glu Leu Gly Lys Ser Pro Leu Thr His Tyr Thr Ile Phe Trp Thr Asn
            530                 535                 540

Ala Gln Asn Gln Ser Phe Ser Ala Ile Leu Asn Ala Ser Ser Arg Gly
545                 550                 555                 560

Phe Val Leu His Gly Leu Glu Pro Ala Ser Leu Tyr His Ile His Leu
                565                 570                 575

Met Ala Ala Ser Gln Ala Gly Ala Thr Asn Ser Thr Val Leu Thr Leu
            580                 585                 590

Met Thr Leu Thr Pro Glu Gly Ser Glu Leu His Ile Ile Leu Gly Leu
            595                 600                 605

Phe Gly Leu Leu Leu Leu Leu Thr Cys Leu Cys Gly Thr Ala Trp Leu
610                 615                 620

Cys Cys Ser Pro Asn Arg Lys Asn Pro Leu Trp Pro Ser Val Pro Asp
625                 630                 635                 640

Pro Ala His Ser Ser Leu Gly Ser Trp Val Pro Thr Ile Met Glu Glu
                645                 650                 655

Leu Pro Gly Pro Arg Gln Gly Gln Trp Leu Gly Gln Thr Ser Glu Met
            660                 665                 670

Ser Arg Ala Leu Thr Pro His Pro Cys Val Gln Asp Ala Phe Gln Leu
            675                 680                 685

Pro Gly Leu Gly Thr Pro Pro Ile Thr Lys Leu Thr Val Leu Glu Glu
            690                 695                 700

Asp Glu Lys Lys Pro Val Pro Trp Glu Ser His Asn Ser Ser Glu Thr
705                 710                 715                 720

Cys Gly Leu Pro Thr Leu Val Gln Thr Tyr Val Leu Gln Gly Asp Pro
                725                 730                 735

Arg Ala Val Ser Thr Gln Pro Gln Ser Gln Ser Gly Thr Ser Asp Gln
            740                 745                 750

Val Leu Tyr Gly Gln Leu Leu Gly Ser Pro Thr Ser Pro Gly Pro Gly
            755                 760                 765

His Tyr Leu Arg Cys Asp Ser Thr Gln Pro Leu Leu Ala Gly Leu Thr
            770                 775                 780

Pro Ser Pro Lys Ser Tyr Glu Asn Leu Trp Phe Gln Ala Ser Pro Leu
785                 790                 795                 800

Gly Thr Leu Val Thr Pro Ala Pro Ser Gln Glu Asp Asp Cys Val Phe
                805                 810                 815

Gly Pro Leu Leu Asn Phe Pro Leu Leu Gln Gly Ile Arg Val His Gly
            820                 825                 830
```

```
Met Glu Ala Leu Gly Ser Phe
        835
```

TREATMENT OF UVEITIS

This application is associated with and claims priority from U.S. Provisional Patent Application No. 61/250,101, filed on 9 Oct. 2009, entitled "Treatment of uveitis", the entire contents of which, are incorporated herein by reference.

FIELD

The present invention relates generally to a method for treating or preventing or otherwise ameliorating the effects of inflammatory conditions of the eye including uveitis.

BACKGROUND

Bibliographic details of references provided in the subject specification are listed at the end of the specification.

Reference to any prior art is not, and should not be taken as an acknowledgment or any form of suggestion that this prior art forms part of the common general knowledge in any country.

Uveitis is a relatively common disease characterized by inflammation of the eye including the iris, ciliary body and the choroid. Sight threatening complications of uveitis include glaucoma, cataracts and retinal detachment. Neutrophils infiltrate into the eye and cause damage by release of inflammatory products such as superoxide and myeloperoxidase (MPO) (Goto et al., *Nippon Ganka Gakkai Zasshi*, 98(10):1019-26, 1994; Yamada et al., *Journal of free radicals in biology & medicine*, 2(2):111-7, 1986; Gritz et al., *Current Eye Research*, 10(10):927-31, 1991; Graff et al., *Journal of pharmacological and toxicological methods*, 39(3):169-78, 1998).

Uveitis is broadly categorized into anterior or posterior uveitis depending on the site of inflammation. Typically, anterior uveitis responds to local steroids, although severe posterior inflammation (particularly in patients with bilateral disease or associated systemic autoimmune disease) often requires systemic corticosteroids and/or agents such as methotrexate, cyclosporine A, or cyclophosphamide. Biologics including interferon and inhibitors of TNF, IL-2 and various adhesion molecules have recently introduced as treatment options. However, in some patients inflammation continues despite these therapies and causes permanent visual loss, or treatment is not tolerated because of side effects (Imrie and Dick, *Current opinion in ophthalmology*, 18(6):481-6, 2007). 5-20% of all blindness results from uveitis and there remains a need for more therapeutic options.

One cytokine involved in inflammatory reactions is granulocyte colony-stimulating factor (G-CSF) which is encoded by the CSF-3 gene. G-CSF is a hemopoietic growth factor that regulates the production of granulocytes (Nicola et al., *Nature* 314:625, 1985; Metcalf, *International Journal of Cancer* 25:225, 1980; Nicola et al., *Journal of Biological Chemistry* 258:9017, 1983). G-CSF mediates its effects through interaction with the G-CSF receptor (G-CSFR, encoded by the CSFR-3 gene), a member of the type I cytokine receptor superfamily (Demetri et al., *Blood* 78:2791-2808, 1991). Major biological actions of G-CSF in humans and mice include increasing the production and release of neutrophils from the bone marrow (Souza et al., *Science* 232:61, 1986; Lord et al., *Proc. Natl. Acad. Sci. USA* 86:9499-9503, 1989), mobilizing hemopoietic progenitor cells from the marrow into the peripheral blood (Bungart et al., *British Journal of Haematology* 22:1156, 1990; de Haan et al., *Blood* 86:2986-2992, 1995; Roberts et al., *Blood* 89:2736-2744, 1997) and modulating the differentiation and effector functions of mature neutrophils (Yong et al., *European Journal of Haematology* 49:251-259, 1992; Colotta et al., *Blood* 80:2012-2020, 1992; Rex et al., *Transfusion* 35:605-611, 1995; Gericke et al., *Journal of Leukocyte Biology* 57:455-461, 1995; Xu et al., *British Journal of Haematology* 93:558-568, 1996; Yong, *British Journal of Haematology* 94:40-47, 1996; Jacob et al., *Blood* 92:353-361, 1998). G-CSF also acts on mature postmitotic neutrophils after they leave the bone marrow including having effects on phagocytosis (Bialek et al., *Infection* 26(6):375-8, 1998), apoptosis (Dibbert et al., *Proc Natl Acad Sci USA* 96(23):13330-5, 1999) and homing (Dagia et al., *Nat Med* 12(10):1185-90, 2006; Eyles et al., *Blood* 112 (13):5193-201, 2008). G-CSF is used to treat neutropenia, as well as to induce mobilization of hemopoietic stem cells (HSC) for autologous and allogenic stem cell transplantation (Welte et al., *Blood* 88:1907-1929, 1996).

There are sporadic reports of patients treated with G-CSF experiencing some level of uveitis (Fraunfelder and Harrison, *Cornea*, 26(3):368-9, 2007; Esmaeli et al., *Cornea*, 21(6): 621-2, 2002; Parkkali et al., *Bone Marrow Transplant*, 17(3): 433-4, 1996; Tsuchiyama et al., *Ann Hematol*, 79(5):269-71, 2000). However, a number of these reports are in respect of patients with previous episodes of autoimmune disease and/or in combination with other treatment. In addition, some patients with autoimmune disease and suffering from uveitis have increased local and systemic G CSF and G-CSFR levels along with other cytokines and chemokines (Takahama et al., *J Dermatol*, 21(8):546-52, 1994; Kawakami et al., *Arch Dermatol*, 140(5):570-4, 2004; Banerjee et al., *Investigative Ophthalmology & Visual Science* 48(5):2203-2207, 2007). Gene expression analysis of cytokines and their receptors after disease induction in a mouse model of uveitis (Hashida et al., *Invest Ophthalmol Vis Sci.*, 46(11):4224-34 2005) showed that a very large number of different cytokines, cytokine receptors, and chemokines were upregulated following disease induction, including G-CSF and its receptor.

There is a need to develop new treatments for uveitis.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present invention relates generally to the use of antagonists of G-CSF, and/or its receptor (G-CSFR) in the treatment of uveitis. By "antagonist" includes inhibiting G-CSF activity, G-CSFR activity, G-CSF/G-CSFR interaction and expression of a genetic locus encoding G-CSF or G-CSFR.

The present invention contemplates, therefore, the inhibition of G-CSF or G-CSFR systemically or locally and/or the down-regulation of expression of a G-CSF or G-CSFR in the treatment of uveitis.

Reference to "G-CSF" or its full name "granulocyte-colony stimulating factor" includes homologs and derivatives of G-CSF. A "homolog" or "derivative" includes polymorphic variants of G-CSF.

The term "G-CSFR" or its full name "granulocyte-colony stimulating factor receptor" includes homologs and derivatives of G-CSFR. A "homolog" or "derivative" includes polymorphic variants of G-CSF.

By "down regulating expression of G-CSF or G-CSFR" includes inhibiting expression of genetic material encoding G-CSF or G-CSFR including inhibiting transcription, translation and/or mRNA processing.

The expression "inhibition of G-CSF or G-CSFR" or "antagonizing G-CSF or G-CSFR" includes inhibiting the activity or signaling function of G-CSF or G-CSFR including inhibiting G-CSF/G-CSFR interaction.

The present invention is directed to the treatment or prophylaxis of inflammatory conditions of the eye including uveitis.

Accordingly, one aspect of the present invention contemplates a method for the treatment of uveitis in a subject, the method comprising administering to the subject an amount of an agent effective to inhibit G-CSF or G-CSFR or down regulate expression of G-CSF or G-CSFR.

In an embodiment, a method is provided for treating uveitis in a subject, the method comprising administering to the subject a G-CSF or G-CSFR inhibiting agent selected from the group consisting of an antibody specific for G-CSF or G-CSFR; a soluble G-CSFR or a G-CSF-binding portion thereof; a 20 to 30 nucleotide sense or antisense molecule targeted to a nucleic acid molecule encoding G-CSF, the nucleic acid molecule comprising the sequence set forth in SEQ ID NO:3; and a 20 to 30 nucleotide sense or antisense molecule targeted to a nucleic acid molecule encoding a G-CSFR, the nucleic acid molecule comprising the sequence set forth in SEQ ID NO:7.

In a particular embodiment, the antagonist is an antibody or a derivative thereof specific for human G-CSFR (hG-CSFR).

Hence, another aspect of the present invention is directed to a method for the treatment of uveitis in a subject, the method comprising administering to the subject an amount of an antibody specific for human G-CSFR.

Generally, the agent is administered for a time and under conditions sufficient to ameliorate the symptoms of uveitis. Such symptoms include inflammation of the eye including iris, ciliary body and choroid as well as complications thereof including glaucoma, cataracts and retinal detachment.

The administration may be systemic or local. Reference to "systemic administration" includes intra-articular, intravenous, intramuscular, intraperitoneal, and subcutaneous injection, infusion, as well as administration via oral, rectal and nasal routes, or via inhalation. Local administration may include administration onto or into the eye including intraocular administration and inter-ocular administration.

The agents which antagonize G-CSF, G-CSFR, G-CSF/G-CSFR signaling or their production include proteinaceous, non-proteinaceous (e.g. chemical entities) and nucleic acid molecules.

Proteinaceous and non-proteinaceous molecules include peptides, polypeptides and proteins, small, intermediate or large chemical molecules as well as molecules identified from natural product screening or the screening of chemical libraries. Natural product screening includes the screening of extracts or samples from plants, microorganisms, soil river beds, coral, aquatic environments and extraterrestrial environments for molecules or groups of molecules which effect G-CSF or G-CSFR activity or the level of G-CSF or G-CSFR expression. These molecules may also affect G-CSF/G-CSFR interaction or otherwise modulate G-CSF/G-CSFR-mediated signaling. In a particular embodiment, the agent is an antibody specific for G-CSF or G-CSFR. The antibody may also be derivatized such as hyumanized or deimmunized. In a most particular embodiment, the agent is an antibody specific for hG-CSFR.

The present invention further contemplates combination therapy such as antagonizing G-CSF and/or G-CSFR in combination with another anti-inflammatory agent, immunosuppressive agent or other agent used in the treatment of uveitis.

Accordingly, another aspect of the present invention relates to a method for the treatment of uveitis in a subject, the method comprising administering an agent which inhibits G-CSF or G-CSFR or inhibits the expression of G-CSF or G-CSFR and at least one other therapeutic agent such as a corticosteroid (e.g. prednisolone, triamcinolone and fluocinolone), a cycloplegic, an immunosuppressive agent (e.g. azathioprine, methotrexate, mycophenolate mofetil, cyclosporine, tacrolimus, cyclophosphamide and chlorambucil), or an immune modulator (e.g. etanercept, infliximab, daclizumab).

As indicated above, one particular G-CSF or G-CSFR antagonizing agent is an antibody which inhibits the activity of G-CSF or G-CSFR or which inhibits G-CSF/G-CSFR interaction. In an embodiment, the antibody specifically or selectively binds to G-CSF or G-CSFR. Other useful agents include small molecule inhibitors, soluble G-CSF receptors or G-CSF-binding fragments thereof, receptor-binding portions of G-CSF and nucleic acid molecules which inhibit G-CSF or G-CSFR expression. The antibody may be monospecific or multi-specific including bi-specific.

Hence, in an embodiment, the present invention contemplates a method for the treatment of uveitis in a subject, the method comprising administering to the subject an amount of an antibody effective to inhibit the activity of G-CSF or G-CSFR or the ability for G-CSF to interact with G-CSFR. This aspect of the present invention includes the administration of an antibody effective to inhibit G-CSF/G-CSFR-mediated signaling.

Another aspect of the present invention provides a method for the treatment of uveitis in a subject, the method comprising administering to the subject an amount of an antibody specific for human G-CSFR (hG-CSFR).

Whilst sense or antisense molecules directed to the G-CSF gene or mRNA or G-CSFR gene or mRNA are provided, sense or antisense molecules are also provided against any portion of the coding or non-coding regions including leader sequence and selected introns or exons of the G-CSF or G-CSFR gene or mRNA. Hence, sense and antisense molecules of 20 to 30 nucleotides in length are contemplated herein to one or more of SEQ ID NOs:2, 3, 6 and/or 7.

Useful subjects to be treated are mammals and in particular humans. Hence, the present invention has both human and veterinary applications.

The present invention extends to the use of pharmaceutical compositions comprising antagonists of G-CSF or G-CSFR. One particularly useful composition comprises an anti-G-CSF antibody or an anti-G-CSFR antibody. As indicated above, an antagonist of G-CSF or G-CSFR includes an antagonist of G-CSF or G-CSFR activity as well as G-CSF/G-CSFR intervention.

The present invention further contemplates the use of an antibody to G-CSF or G-CSFR in the manufacture of a medicament for the treatment of uveitis in a subject.

Another aspect provides for the use of an agent which inhibits the activity of G-CSF or G-CSFR or which inhibits expression of a gene encoding G-CSF or G-CSFR, wherein the agent is selected from the group consisting of an antibody specific for G-CSF or G-CSFR; a soluble G-CSFR or a G-CSF-binding portion thereof; a 20 to 30 nucleotide sense or antisense molecule targeted to a nucleic acid molecule encoding G-CSF, said nucleic acid molecule comprising the sequence set forth in SEQ ID NO:3; and a 20 to 30 nucleotide sense or antisense molecule targeted to a nucleic acid molecule encoding a G-CSFR, the nucleic acid molecule comprising the sequence set forth in SEQ ID NO:7, in the manufacture of a medicament for the treatment of uveitis in a subject.

In a particular embodiment, the presnet invention is directed to the use of an antibody hG-CSFR in the manufacture of a medicament for the treatment of uveitis in a subject.

An agent is also provided which inhibits the activity of G-CSF or G-CSFR or which inhibits expression of a gene encoding G-CSF or G-CSFR, wherein the agent is selected from the group consisting of an antibody specific for G-CSF or G-CSFR; a soluble G-CSFR or a G-CSF-binding portion thereof; a 20 to 30 nucleotide sense or antisense molecule targeted to a nucleic acid molecule encoding G-CSF, the nucleic acid molecule comprising the sequence set forth in SEQ ID NO:3; and a 20 to 30 nucleotide sense or antisense molecule targeted to a nucleic acid molecule encoding a G-CSFR, the nucleic acid molecule comprising the sequence set forth in SEQ ID NO:7 for use in the treatment of uveitis in a subject.

In an embodiment, the agent is an antibody specific for G-CSF or G-CSFR such as hG-CSFR.

A summary of sequence identifiers used throughout the subject specification is provided in Table 1. A list of abbreviations is provided in Table 2.

TABLE 1

Summary of sequence identifiers

| Sequence ID No. | Description |
|---|---|
| 1 | Human G-CSF amino acid sequence including the leader sequence |
| 2 | Human G-CSF coding and non-coding nucleotide sequence |
| 3 | Human G-CSF nucleotide sequence encoding mature protein |
| 4 | Human G-CSF mature protein amino acid sequence |
| 5 | Human G-CSFR3 amino acid sequence including the leader sequence |
| 6 | Human G-CSF3R coding and non-coding nucleotide sequence |
| 7 | Human G-CSF3R nucleotide sequence encoding mature protein |
| 8 | Human G-CSF3R mature protein amino acid sequence |

TABLE 2

Abbreviations

| Abbreviation | Definition |
|---|---|
| Anti-hG-CSF antibody | An antibody specific for human G-CSF |
| Anti-hG-CSF receptor antibody | An antibody specific for human G-CSFR |
| EAU | Experimental autoimmune uveitis |
| G-CSF | Granulocyte-colony stimulating factor |
| G-CSFR | Granulocyte-colony stimulating factor receptor |
| hG-CSF | Human granulocyte-colony stimulating factor |
| hG-CSFR | Human granulocyte-colony stimulating factor recepto |
| HSC | Hemopoietic stem cell |

DETAILED DESCRIPTION

Figure 1:
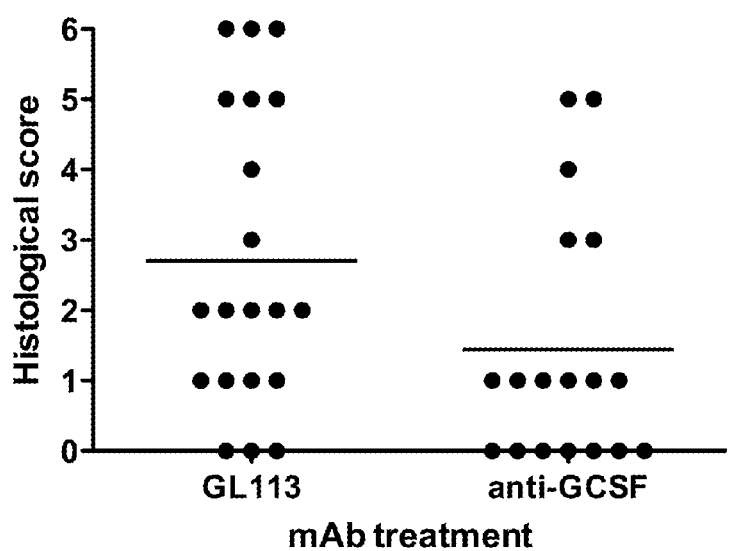
FIG. 1 is a graphical representation showing histological scores at day 21 in anti-G-CSF or isotype control antibody treated animals. Antibodies were given every second day from day 8 to day 20 after EAU induction. Eyes were examined by histology and were scored from 0 (no disease) to 6 (severe disease) as noted in the experimental section. n=10 mice, p<0.05, scored blinded.

The singular forms "a", "an" and "the" include plural aspects unless the context clearly dictates otherwise. Thus, for example, reference to "a G-CSF or G-CSFR inhibiting agent" includes a single agent as well as two or more agents; reference to "an antibody" includes a single antibody, as well as two or more antibodies; reference to "the invention" includes single and multiple aspects of an invention; and so forth.

The present invention contemplates the treatment or prophylaxis of an inflammatory condition of the eye, including uveitis, using an agent which inhibits G-CSF or G-CSF activity or interaction or inhibiting expression of a genetic locus encoding G-CSF or G-CSFR.

The terms such as "agent", "compound", "active", "medicament" and "therapeutic" may be used interchangeably herein to refer to a substance that induces a desired pharmacological and/or physiological effect of antagonizing G-CSF, G-CSFR, G-CSF/G-CSFR interaction, G-CSF/G-CSFR-mediated signaling and/or expression of loci encoding G-CSF or G-CSFR. The terms also encompass pharmaceutically acceptable and pharmacologically active forms thereof, including salts. Hence, the desired effect includes the inhibition of G-CSF activity or signaling or function and down regulation of expression of G-CSF or its receptor. By "down regulation of expression" includes "inhibition of expression" and means inhibiting or preventing or reducing transcription or translation or RNA processing leading to G-CSF or G-CSFR production. Hence, any form of reduction in G-CSF and/or G-CSFR levels is contemplated herein.

Agents are contemplated herein which antagonize G-CSF or G-CSFR and include an antibody specific for G-CSF or G-CSFR; a soluble G-CSFR or a G-CSF-binding portion thereof; a 20 to 30 nucleotide sense or antisense molecule targeted to a nucleic acid molecule encoding G-CSF, the nucleic acid molecule comprising the sequence set forth in SEQ ID NO:3; and/or a 20 to 30 nucleotide sense or antisense molecule targeted to a nucleic acid molecule encoding a G-CSFR, the nucleic acid molecule comprising the sequence set forth in SEQ ID NO:7.

Combination therapy involving the use of a G-CSF or G-CSFR antagonist together with another therapeutic agent such as an anti-inflammatory, an immunosuppressive agent and/or an other agent used in the treatment of uveitis is also contemplated by the present invention.

One particularly useful agent is an antibody specific or selective for a G-CSF or G-CSFR and/or which prevents or at least antagonizes G-CSF/G-CSFR interaction. In an embodiment, the antibody is specific for G-CSFR including hG-CSFR.

The terms "antibody" and "antibodies" include polyclonal and monoclonal antibodies and all the various forms derived from monoclonal antibodies, including but not limited to full-length antibodies (e.g. having an intact Fc region), antigen-binding fragments, including for example, Fv, Fab, Fab' and F(ab')$_2$ fragments; and antibody-derived polypeptides produced using recombinant methods such as single chain antibodies. The terms "antibody" and "antibodies" as used herein also refer to human antibodies produced for example in transgenic animals or through phage display, as well as chimeric antibodies, humanized antibodies, primatized antibodies or deimmunized antibodies. It also includes other forms of antibodies that may be therapeutically acceptable and antigen-binding fragments thereof, for example single domain antibodies derived from cartilage marine animals or Camelidae, or from libraries based on such antibodies. The selection of fragment or modified forms of the antibodies may also involve any effect the fragments or modified forms have on their half-lives. For example, it may in certain circumstances be advantageous for an antibody to have a short half-life to avoid global affects of anti-G-CSF/G-CSFR treatment, such as neutropenia. Alternatively, where exacerbations are common or likely, an antibody with a longer half-life may be advantageous. A "half-life" for an antibody is considered herein to be short if it is within 2 days or less. A longer half-life for an antibody would be any half-life in excess of 2 days and more particularly may be greater than 7 days.

The term "monoclonal antibody" is used herein to refer to an antibody obtained from a population of substantially homogeneous antibodies. That is, the individual antibodies comprising the population are identical except for naturally occurring mutations that may be present in minor amounts. The modifier "monoclonal" as used herein therefore indicates the character of the antibody as being obtained from a substantially homogeneous population of antibodies, and is not used to indicate that the antibody was produced by a particular method. For example, monoclonal antibodies in accordance with the present invention may be made by the hybridoma method described by Kohler and Milstein, *Nature* 256: 495-499, 1975, or may be made by recombinant DNA methods (such as described in U.S. Pat. No. 4,816,567). Monoclonal antibodies may also be isolated from phage antibody libraries using the techniques described in Clackson et al., *Nature* 352:624-628, 1991 or Marks et al., *J. Mol. Biol.* 222:581-597, 1991.

The terms "effective amount" and "therapeutically effective amount" as used herein mean a sufficient amount of an agent which provides the desired therapeutic or physiological effect or outcome, inhibiting G-CSF or G-CSFR or which inhibits expression of G-CSF or G-CSFR. In addition, the effect may be an amelioration of the symptoms of uveitis. Undesirable effects, e.g. side effects, may sometimes manifest along with the desired therapeutic effect; hence, a practitioner balances the potential benefits against the potential risks in determining what is an appropriate "effective amount". The exact amount of agent required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using routine experimentation. For example, the ability of an anti-G-CSF/G-CSFR antibody to ameliorate the effects of uveitis can be evaluated in an animal model system. One of ordinary skill in the art would be able to determine the required amounts based on such factors as the subject's size, the severity of the subject's symptoms, and the particular composition or route of administration selected.

Insofar as one embodiment of the present invention relates to the use of antibodies to G-CSF or its receptor, the effective amount include from about 10 μg/kg body weight to 20 mg/kg body weight of antibody such as 10, 20, 30, 40, 50, 60, 70, 80, 90, 100 μg/kg body weight, 100, 200, 300, 400, 500, 600, 700, 800, 900, 1000 μg/kg body weight or 2, 3, 4, 5, 6, 7, 8, 9, 10, 11, 12, 13, 14, 15, 16, 17, 18, 19 or 20 mg/kg body weight. Similar amount are provided for single or combination therapy.

Generally, the agent is provided with a pharmaceutically or pharmacologically acceptable carrier, diluent or excipient.

A "pharmaceutically acceptable" carrier, diluent and/or excipient is a pharmaceutical vehicle comprised of a material that is not biologically or otherwise undesirable, i.e. the material may be administered to a subject along with the selected G-CSF/G-CSFR-antagonizing agent without causing any or a substantial adverse reaction. Carriers may include any and all solvents, dispersion media, antibacterial and antifungal agents, agents used for adjusting tonicity, buffers, chelating agents, and the like.

Similarly, a "pharmacologically acceptable" salt of an agent as provided herein is a salt, that is not biologically or otherwise undesirable.

The terms "treating" and "treatment" as used herein refer to therapeutic treatment and may include prophylactic or preventative measures. For example, treatment may result in a reduction in severity and/or the frequency of symptoms of the uveitis in some subjects, the elimination of symptoms and/or underlying cause of the condition, the prevention of the occurrence of symptoms of the condition and/or their underlying cause and improvement or remediation or amelioration of damage following the inflammatory condition. Hence, the treatment may not result in a "cure" but rather an amelioration of symptoms.

The antibodies may also be chimeric which include antibodies to G-CSF or G-CSFR comprising the heavy and light chain variable regions of rat or rabbit antibodies to G-CSF or G-CSFR and human heavy and light chain constant domains.

The terms "condition" and "disease" are used interchangeably throughout the subject specification.

A "subject" as used herein refers to an animal, particularly a mammal and more particularly a human who can benefit from the pharmaceutical compositions and methods of the present invention. There is no limitation on the type of animal that could benefit from the presently described pharmaceutical compositions and methods. A subject regardless of whether a human or non-human animal may be referred to as an individual, patient, animal, host or recipient as well as subject. The compounds and methods of the present invention have applications in human medicine and veterinary medicine.

Particular mammals are humans and laboratory test animals. Examples of laboratory test animals include mice, rats, rabbits, guinea pigs, hamsters, cats and dogs and primates.

One particularly useful agent of the present invention is an antibody to either G-CSF or G-CSFR that inhibits G-CSF signalling through the G-CSF receptor. In an example, the antibody is specific for hG-CSFR. Antibodies to G-CSF may be referred to as anti-G-CSF antibodies, and antibodies to G-CSFR may be referred to as anti-G-CSFR antibodies. Where it is intended to refer to either an anti-G-CSF antibody or an anti-G-CSFR antibody it may simply refer to an anti-G-CSF/G-CSFR antibody or antibodies.

Although both polyclonal and monoclonal antibodies can be readily produced monoclonal antibodies are particularly preferred as they can be generated in large quantities, are highly specific and are directed against a single antigenic site. Furthermore, the monoclonal antibody preparations are homogeneous, making them ideal for generating antigen-binding fragments and other engineered antibody derivatives for therapeutic applications.

Although polyclonal antibodies are also relatively easily prepared, they are not as useful as monoclonal antibodies as polyclonal antibody preparations typically include different antibodies directed against different antigenic sites and thus are not as suitable for generating antigen-binding fragments and other engineered antibody derivatives for therapeutic applications.

The hybridoma method described above is used in animals, such as mice, to produce monoclonal antibodies. However, antibodies derived from animals are generally unsuitable for administration to humans as they may cause an immune response. As described below, such antibodies may be modified to become suitable for administration to humans or the desired non-human subject.

The anti-G-CSF/G-CSFR antibodies, for example, may also be produced using recombinant methods (for example, in an E. coli expression system) well known in the art. In this approach, DNA encoding monoclonal antibodies, such as the murine monoclonal antibodies of the present invention, may be isolated from the hybridoma cell lines, sequenced using standard procedures and optionally manipulated using recombinant DNA technology. For example, the DNA may be fused to another DNA of interest, or altered (such as by mutagenesis or other conventional techniques) to add, delete, or substitute one or more nucleic acid residues. The DNA may be placed into vectors which are then transfected or transformed into appropriate host cells using methods well known in the art (such as described in U.S. Pat. Nos. 4,399,216; 4,912,040; 4,740,461 and 4,959,455). The DNA isolated from the hybridoma cell lines may also be modified to change the character of the antibody produced by its expression.

For example, chimeric forms of murine anti-G-CSF/G-CSFR monoclonal antibodies may be produced by replacing the nucleotides encoding selected murine heavy and light chain constant domains with nucleotides encoding human heavy and light chain constant domains, such as is described in U.S. Pat. No. 4,816,567 and by Morrison et al., *Proc. Nat. Acad. Sci.* 81:6851, 1984. The chimeric antibodies may then be produced in an appropriate cell line, such as a murine myeloma cell line, that has been transfected with modified DNA.

Thus, among the antibodies contemplated by the present invention are chimeric anti-G-CSF or G-CSFR antibodies that comprise the heavy and light chain variable regions of a murine anti-G-CSF/G-CSFR monoclonal antibody fused to non-murine heavy and light chain antibody constant domains. In a particular embodiment, the non-murine heavy and light chain constant domains are human heavy and light chain antibody constant domains. Similarly, chimeric antibodies may include antibodies to G-CSF or G-CSFR comprising the heavy and light chain variable regions of rat or rabbit antibodies to G-CSF or G-CSFR and human heavy and light chain constant domains.

The anti-G-CSF or G-CSFR antibodies for use in the present invention also include humanized antibodies. In general, humanized antibodies are human antibodies (the recipient antibody) in which the complementarity determining (CDR) region residues have been replaced by CDR region residues from a non-human species (the donor antibody), such as from a mouse, rat, rabbit or non-human primate. In some cases, certain framework region (FR) residues of the human antibody may also be replaced by corresponding non-human residues, or the humanized antibodies may comprise residues which are not found in the recipient antibody or in the donor antibody. These modifications are made to enhance antibody performance and affinity. In general, the humanized antibody will comprise substantially all of at least one, and typically two, variable regions, in which all or substantially all of the CDR regions correspond to those of a non-human antibody, and all or substantially all of the FRs are those of a human antibody sequence. The humanized antibody may also optionally comprise at least a portion of an antibody constant region (Fc), typically that of a human antibody (Jones et al., *Nature* 321:522-525, 1986; Reichmann et al., *Nature* 332: 323-329, 1988; Presta, *Curr. Op. Struct. Biol.* 2:593-596, 1992; Liu et al., *Proc. Natl. Acad. Sci. USA* 84:3439, 1987; Larrick et al., *Bio/Technology* 7:934, 1989; Winter & Harris, *TIPS* 14:139, 1993; Carter et al., *Proc. Nat. Acad. Sci.* 89:4285 1992). Similarly, to create a primatized antibody the murine CDR regions can be inserted into a primate framework using methods known in the art (see e.g. WO 93/02108 and WO 99/55369).

Alternatively, a humanized antibody may be created by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan et al., *Mol. Immunol.* 28:489-498, 1991 and Pedersen et al., *J. Mol. Biol.* 235:959-973, 1994). Therefore, it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable region "invisible" to the human immune system. This procedure of humanization is referred to as "veneering" because only the surface of the antibody is altered, the supporting residues remain undisturbed.

Further, WO 2004/006955 describes methods for humanizing antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO 2004/006955, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies.

The CDRs of a given antibody may be readily identified, for example using the system described by Kabat et al in *Sequences of Proteins of Immunological Interest*, 5th Ed., US Department of Health and Human Services, PHS, NIH, NIH Publication No. 91-3242, 1991).

In a particular embodiment, the antibodies for use in the present invention are human monoclonal antibodies. Such human monoclonal antibodies directed against G-CSF or G-CSFR can be generated using transgenic or transchromosomic mice carrying parts of the human immune system rather than the mouse system. These transgenic and transchromosomic mice include mice referred to herein as HuMAb mice and KM mice.

Still further, alternative transgenic animal systems expressing human immunoglobulin genes are available in the art and can be used to raise antibodies. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963.

Moreover, alternative transchromosomic animal systems expressing human immunoglobulin genes are available in the art and can be used to raise antibodies against G-CSF or G-CSFR. For example, mice carrying both a human heavy chain transchromosome and a human light chain transchromosome, referred to as "TC mice" can be used; such mice are described in Tomizuka et al., *Proc. Natl. Acad. Sci. USA* 97:722-727, 2000.

Human monoclonal antibodies can also be prepared using phage display methods for screening libraries of human immunoglobulin genes. Such phage display methods for isolating human antibodies are established in the art. See for example: U.S. Pat. Nos. 5,223,409; 5,403,484; and 5,571,698; U.S. Pat. Nos. 5,427,908 and 5,580,717; U.S. Pat. Nos. 5,969,108 and 6,172,197 and U.S. Pat. Nos. 5,885,793; 6,521,404; 6,544,731; 6,555,313; 6,582,915 and 6,593,081.

Human monoclonal antibodies can also be prepared using SCID mice into which human immune cells have been reconstituted such that a human antibody response can be generated upon immunization. Such mice are described in, for example, U.S. Pat. Nos. 5,476,996 and 5,698,767. The anti-G-CSF/G-CSFR antibodies of the present invention also include antigen-binding fragments such as Fv, Fab, Fab' and F(ab')$_2$ fragments. Traditionally, antigen-binding fragments were generated by the proteolytic digestion of full antibodies (Morimoto et al., *Journal of Biochemical and Biophysical Methods* 24:107-117, 1992; Brennan et al., *Science* 229:81, 1985). A number of recombinant methods have now been developed for producing antigen-binding fragments of antibodies directly in recombinant host cells.

For example, Fab'-SH fragments can be directly recovered from *E. coli* and chemically coupled to form F(ab')$_2$ fragments (Carter et al., *Bio/Technology* 10:163-167, 1992). F(ab')$_2$ fragments can also be formed using the leucine zipper GCN4 to promote assembly of the F(ab')$_2$ molecule. Fv, Fab or F(ab')$_2$ fragments can also be isolated directly from recombinant host cell cultures. A number of recombinant methods have been developed for the production of single chain antibodies including those described in U.S. Pat. No. 4,946,778; Bird, *Science* 242:423, 1988, Huston et al., *Proc. Natl. Acad. Sci. USA* 85:5879, 1988 and Ward et al., *Nature* 334:544, 1989. Single chain antibodies may be formed by linking heavy ($V_H$) and light ($V_L$) chain variable region (Fv region) fragments via an short peptide linker to provide a single polypeptide chain (scFvs). The scFvs may also form dimers or trimers, depending on the length of a peptide linker between the two variable regions (Kortt et al., *Protein Engineering* 10:423, 1997). Phage display is another well known recombinant method for producing the antigen-binding fragments of the present invention.

The antigen-binding fragments of the present invention may be screened for desired properties. The assays described herein provide the means to identify antigen-binding fragments that bind to G-CSF or G-CSFR and which antagonize G-CSF signaling through G-CSFR.

Mammalian cell lines available as hosts for expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g. Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9. cells, amphibian cells, bacterial cells, plant cells and fungal cells. When recombinant expression vectors encoding the heavy chain or antigen-binding portion thereof, the light chain and/or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention from host cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

Antibodies expressed by different cell lines or in transgenic animals may have different glycosylation patterns from each other. However, all such antibodies to G-CSF or G-CSFR used in the treatment of uveitis are part of the present invention, regardless of the glycosylation pattern of the antibodies.

Techniques are also known for deriving an antibody of a different subclass or isotype from an antibody of interest, i.e. subclass switching. Thus, IgG1 or IgG4 monoclonal antibodies may be derived from an IgM monoclonal antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g. DNA encoding the constant region of an antibody of the desired isotype.

Vectors available for cloning and expression in host cell lines are well known in the art, and include but are not limited to vectors for cloning and expression in mammalian cell lines, vectors for cloning and expression in bacterial cell lines, vectors for cloning and expression in phage and vectors for cloning and expression insect cell lines. The antibodies can be recovered using standard protein purification methods.

In a particular embodiment, antibodies for use in the method of the present invention are human or humanized anti-G-CSF/G-CSFR antibodies which antagonize G-CSF signaling via G-CSFR.

Particularly, the human or humanized anti-G-CSF/G-CSFR antibodies are in isolated, homogenous or fully or partially purified form.

More particularly, the human or humanized anti-G-CSF/G-CSFR antibodies are full-length monoclonal antibodies or antigen-binding fragments.

As indicated above, the selection of antigen-binding fragments or modified forms of the antibodies may be influenced by the effect the fragments or modified forms have on the individual half-life.

In a particular embodiment, antibodies and antibody fragments selected as being particularly suitable for delivery to the eye are selected for use in the method of the present invention. For example, U.S. Pat. No. 6,773,916 teaches that sub-immunoglobulin antigen-binding molecules, for example antibody fragments such as single chain antibodies, are particularly suitable for delivery to the eye. WO2008006235 teaches methods of generating antibody fragments that permeate the eye, and WO2009000098 and WO2009000099 teach further methods of modifying the properties of antibodies to enhance their suitability for delivery to the eye. Delivery may be inter alia by injection, eye drops, eye spray, eye wash, eye ointment and the like.

Another example of a useful agent is a soluble form of the G-CSFR which competes with the naturally occurring membrane-associated G-CSFR for G-CSF interaction. Those skilled in the art can readily prepare soluble forms of the receptor, see for example U.S. Pat. No. 5,589,456 and Honjo et al., *Acta Crystallograph Sect F Struct Biol Cryst Commun.* 61(Pt 8):788-790, 2005.

Alternatively, agents can be screened for their ability to bind to G-CSF or G-CSFR-genetic materials. In one embodiment, G-CSF- or G-CSFR-encoding cDNA or genomic DNA or mRNA transcript or portion thereof such as an EST or SAGE tag is immobilized to a solid support such as a nanoparticle or microsphere. Potential agents are then brought into contact with the immobilized nucleic acid molecules and binding detected by change in radiation, emissions, atom excitation, mass and/or density.

Once identified, the agent is eluted off the nucleic acid molecule and characterized in more detail. For example, agents which bind to G-CSF/G-CSFR genetic material may inhibit expression (transcription and/or translation).

The present invention further contemplates using chemical analogs of G-CSF or G-CSFR as antagonists of G-CSF or its receptor. As indicated above, soluble G-CSF receptors may also be employed.

Chemical analogs contemplated herein include, but are not limited to, modifications of side chains, incorporation of unnatural amino acids and/or their derivatives during peptide, polypeptide or protein synthesis and the use of crosslinkers and other methods which impose conformational constraints on the proteinaceous molecule or their analogs.

Yet another aspect of the present invention contemplates the use of an agent including an antibody which competes for binding of an antibody specific for G-CSF or G-CSFR.

Still yet another aspect of the present invention contemplates the use of an antibody specific for hG-CSF in the manufacture of a medicament for the treatment of uveitis in a subject.

Other agents contemplated by the present invention include nucleic acid molecules such as RNA or DNA which are useful for inducing silencing by antisense- or sense-mediated mechanisms of genes encoding the cytokines or their receptors. Sense-mediated gene silencing is also referred to as co-suppression and involves a range of mechanisms including the induction of RNAi. Transcriptional and post transcriptional gene silencing is therefore, contemplated by the present invention.

The terms "nucleic acids", "nucleotide" and "polynucleotide" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog (such as the morpholine ring), internucleotide modifications such as uncharged linkages (e.g. methyl phosphonates, phosphotriesters, phosphoamidates, carbamates, etc.), charged linkages (e.g. phosphorothioates, phosphorodithioates, etc.), pendent moieties (e.g. polypeptides), intercalators (e.g. acridine, psoralen, etc.), chelators, alkylators and modified linkages (e.g. α-anomeric nucleic acids, etc.). Also included are synthetic molecules that mimic polynucleotides in their ability to bind to a designated sequence via hydrogen binding and other chemical interactions. Such molecules are known in the art and include, for example, those in which peptide linkages substitute for phosphate linkages in the backbone of the molecule.

Antisense polynucleotide sequences, for example, are useful in silencing transcripts of the G-CSF genetic sequence or the G-CSFR genetic sequence (see Geng et al., *Molecular Immunology* 44:5121-529, 2007). Furthermore, polynucleotide vectors containing all or a portion of the G-CSF gene locus may be placed under the control of a promoter in either the sense or antisense orientation and introduced into a cell. Expression of such a sense or antisense construct within a cell interferes with target transcription and/or translation. Furthermore, co-suppression (i.e. using sense-suppression) and mechanisms to induce RNAi or siRNA may also be employed. Alternatively, antisense or sense molecules may be directly administered. In this latter embodiment, the antisense or sense molecules may be formulated in a composition and then administered by any number of means to target cells.

A variation on antisense and sense molecules involves the use of morpholinos, which are oligonucleotides composed of morpholine nucleotide derivatives and phosphorodiamidate linkages (for example, Summerton and Weller, *Antisense and Nucleic Acid Drug Development* 7:187-195, 1997).

In one embodiment, the present invention employs compounds such as oligonucleotides and similar species for use in modulating the function or effect of nucleic acid molecules encoding G-CSF or G-CSFR, i.e. the oligonucleotides induce transcriptional or post-transcriptional gene silencing. This is accomplished by providing oligonucleotides which specifically hybridize with one or more nucleic acid molecules encoding the target nucleic acid. The oligonucleotides may be provided directly to a cell or generated within the cell. As used herein, the terms "target nucleic acid" and "nucleic acid molecule encoding G-CSF or G-CSFR" have been used for convenience to encompass the encoding DNA, RNA (including pre-mRNA and mRNA or portions thereof) transcribed from such DNA, and also cDNA derived from such RNA. The hybridization of a compound of the subject invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired.

"Complementary" as used herein, refers to the capacity for precise pairing between two nucleobases of an oligomeric compound. For example, if a nucleobases at a certain position of an oligonucleotide (an oligomeric compound), is capable of hydrogen bonding with a nucleobases at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid. One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products.

In the context of the subject invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those herein described. The antisense and sense oligonucleotides contemplated herein may be synthetic or DNA-derived. The latter includes expression vectors which produce the oligonucleotides after transfection in a target cell.

For topical delivery of antisense compounds, these oligonucleotides may contain modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Particular modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

Sense and antisense nucleotides sequences contemplated herein particularly include 20 to 30 nucleotide bases in length. Reference to "20 to 30" includes 20, 21, 22, 23, 24, 25, 26, 27, 28, 29 or 30 or their equivalents outside the range 20 to 30 nucleotides. The terms "nucleobases" and "nucleotides" may be used interchangeably. Particularly useful sense and antisense molecules are directed to the G-CSF gene or mRNA (SEQ ID NOs:2 and 3) encoding the mature protein (SEQ ID NO:4) or to the G-CSFR gene or mRNA (SEQ ID NOs:6 and 7) encoding the mature protein (SEQ ID NO:8).

Whilst sense or antisense molecules directed to the G-CSF gene or mRNA or G-CSFR gene or mRNA sense or antisense molecules are contemplated against any portion of the coding or non-coding regions including leader sequence and selected introns or extons of the G-CSF or G-CSFR gene or mRNA. Hence, sense and antisense molecules of 20 to 30 nucleotide basis in length are contemplated to one or more of SEQ ID NOs: 2, 3, 6 or 7.

In an alternative embodiment, genetic constructs including DNA "vaccines" are used to generate antisense or sense molecules in mammalian cells. Furthermore, many of the preferred features described above are appropriate for sense nucleic acid molecules.

This aspect of the present invention can be worked implemented by conventional molecular biology and recombinant DNA techniques. The techniques are well known in the art and are described in various publications, such as Sambrook, Fritsch & Maniatis, *Molecular Cloning: A Laboratory Manual*, Second Edition (1989) Cold Spring Harbor Laboratory Press, Cold Spring Harbor, N.Y.; DNA Cloning: *A Practical Approach*, Volumes I and II, D. N. Glover ed. 1985 and Ausubel et al. (eds.), *Current Protocols in Molecular Biology*, John Wiley & Sons, Inc., 1994.

Nucleic acids of the present invention may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

A "promoter" or "promoter sequence" is a DNA regulatory region capable of binding an RNA polymerase in a cell and initiating transcription of a coding sequence. A promoter sequence is generally bounded at its 3' terminus by the transcription initiation site and extends upstream in the 5' direction to include the minimum number of bases or elements necessary to initiate transcription at any level. A transcription initiation site as well as protein binding domains (consensus sequences) responsible for the binding of RNA polymerase may be found within the promoter sequence. The promoter may be operably associated with other expression control sequences, including enhancer and repressor sequences or with a nucleic acid of the invention. Promoters which may be used to control gene expression include, but are not limited to, cytomegalovirus (CMV) promoter and the SV40 early promoter region.

A coding sequence is "under the control of", "functionally associated with" or "operably associated with" transcriptional and translational control sequences in a cell when the sequences direct RNA polymerase mediated transcription of the coding sequence into RNA, preferably mRNA, which then may be trans-RNA spliced (if it contains introns) and, optionally, translated into a protein encoded by the coding sequence.

The terms "express" and "expression" mean allowing or causing the information in a gene, RNA or DNA sequence to be converted into a product; for example, producing a protein by activating the cellular functions involved in transcription and translation of a nucleotide sequence. A DNA sequence is expressed in or by a cell to form an "expression product" such as RNA (such as mRNA or a double stranded short RNA, hairpin RNA or antisense RNA) or a protein (such as an antagonist of cytokine activity or portion of an anti-cytokine antibody). The expression product itself may also be said to be "expressed" by the cell.

The terms "vector", "cloning vector" and "expression vector" mean the vehicle (such as a plasmid) by which a DNA or RNA sequence can be introduced into a host cell, so as to transform the host and, optionally, promote expression and/or replication of the introduced sequence.

The term "transfection" or "transformation" means the introduction of a nucleic acid into a cell. These terms may refer to the introduction of a nucleic acid encoding a cytokine cross-reactive antibody or a fragment thereof into a cell. A host cell that receives the introduced DNA or RNA has been "transformed" and is a "transformant" or a "clone". The DNA or RNA introduced to a host cell can come from any source, including cells of the same genus or species as the host cell, or cells of a different genus or species.

The term "host cell" means any cell of any organism that is selected, modified, transfected, transformed, grown, or used or manipulated in any way, for the production of a substance by the cell, for example the expression of a protein or the replication of a gene.

The term "expression system" means a host cell and compatible vector which, under suitable conditions, can express a protein or nucleic acid which is carried by the vector and introduced to the host cell. Common expression systems include *E. coli* host cells and plasmid vectors, insect host cells and Baculovirus vectors, and mammalian host cells and vectors.

Agents (e.g. antibodies, proteins such as non-signalling mutant forms of G-CSF, small chemical molecules, soluble receptors, etc) identified in accordance with the present invention are conveniently supplied in pharmaceutical compositions.

Composition forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include agents to adjust tonicity, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

Compositions suitable for delivery to the eye may be particularly useful and in this regard where the antagonists of G-CSF or G-CSFR is an antibody or antibody fragment then the sub-immunoglobulin antigen-binding molecules as taught by U.S. Pat. No. 6,773,916, for example antibody fragments such as single chain antibodies, may be helpful. Compositions suitable for delivery to the eye may be designed for topical application, periocular injection or administration by other parenteral routes.

When the modulator is suitably protected, it may be orally administered, for example, with an inert diluent or with an assimilable edible carrier, or it may be enclosed in hard or soft shell gelatin capsule, or it may be compressed into tablets, or it may be incorporated directly with the food of the diet or administered via breast milk. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of modulator. The percentage of the compositions and preparations may, of course, be varied and may conveniently be between about 5 to about 80% of the weight of the unit. The amount of modulator in such therapeutically useful compositions is such that a suitable dosage will be obtained. Preferred compositions or preparations according to the present invention are prepared so that an oral dosage unit form contains between about 0.1 µg and 200 mg of modulator. Alternative dosage amounts include from about 1 µg to about 1000 mg and from about 10 µg to about 500 mg. These dosages may be per individual or per kg body weight. Administration may be per hour, day, week, month or year.

The tablets, troches, pills, capsules, creams and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and anti-fungal agents, isotonic and absorption delaying agents and the like. The use of such media and agents for pharmaceutical active agents is well known in the art and except insofar as any conventional media or agent is incompatible with the modulator, their use in the therapeutic compositions is contemplated. Supplementary active compounds can also be incorporated into the compositions.

As indicated above, administration may be by any means.

Dosage regimens may be adjusted to provide the optimum desired response (e.g. a therapeutic response). For example, a single bolus may be administered, several divided doses may be administered over time or the dose may be proportionally reduced or increased as indicated by exigencies of the therapeutic situation. It is especially advantageous to formulate parenteral compositions in dosage unit form for ease of administration and uniformity of dosage.

A physician or veterinarian having ordinary skill in the art can readily determine and prescribe the effective amount of the pharmaceutical composition required. For example, the physician or veterinarian could start doses of the anti-G-CSF/G-CSFR antibody of the present invention, employed in the pharmaceutical composition at levels lower than that required in order to achieve the desired therapeutic effect and gradually increase the dosage until the desired effect is achieved. In general, a suitable daily dose of a composition of the invention may be that amount of the compound which is the lowest dose effective to produce a therapeutic effect. Such an effective dose will generally depend upon the factors described above. It is preferred that administration be by injection, preferably proximal to the site of the target (e.g. lung). If desired, the effective daily dose of a pharmaceutical composition may be administered as two, three, four, five, six or more subdoses administered separately at appropriate intervals throughout the day.

For therapeutic applications, the anti-G-CSF/G-CSFR antibodies are administered to a mammal, preferably a human, in a pharmaceutically acceptable dosage form such as those discussed above, including those that may be administered to a human intravenously as a bolus or by continuous infusion over a period of time.

The composition may also comprise genetic molecules such as a vector capable of transfecting target cells where the vector carries a nucleic acid molecule capable of encoding a modulator, when the modulator is a proteinaceous molecule. The vector may, for example, be a viral vector. In this regard, a range of gene therapies are contemplated by the present invention including isolating certain cells, genetically manipulating and returning the cell to the same subject or to a genetically related or similar subject.

Hence, the present invention further contemplates a method for the treatment of uveitis in a subject, the method comprising administering to the subject an amount of an agent effective to inhibit G-CSF or G-CSFR or inhibit expression G-CSF or G-CSFR.

The present invention also provides a method for treating uveitis in a subject, the method comprising administering to the subject a G-CSF or G-CSFR inhibiting agent selected from the group consisting of an antibody specific for G-CSF or G-CSFR; a soluble G-CSFR or a G-CSF-binding portion thereof; a 20 to 30 nucleotide sense or antisense molecule targeted to a nucleic acid molecule encoding G-CSF, the nucleic acid molecule comprising the sequence set forth in SEQ ID NO:3; and a 20 to 30 nucleotide sense or antisense molecule targeted to a nucleic acid molecule encoding a G-CSFR, the nucleic acid molecule comprising the sequence set forth in SEQ ID NO:7.

Another aspect provides a method for treating uveitis, the method comprising administering to the subject a G-CSF or G-CSFR inhibiting agent selected from the group consisting of:
  a. an antibody specific for G-CSF;
  b. an antibody specific for G-CSFR;
  c. a soluble G-CSFR or a G-CSF-binding portion thereof;
  d. a 20 to 30 nucleotide sense or antisense molecule targeted to a nucleic acid molecule encoding G-CSF, the nucleic acid molecule comprising the sequence set forth in SEQ ID NO:3; and
  e. a 20 to 30 nucleotide sense or antisense molecule targeted to a nucleic acid molecule encoding a G-CSFR, the nucleic acid molecule comprising the sequence set forth in SEQ ID NO:7.

Another aspect of the present invention relates to a method for the treatment of uveitis in a subject, the method comprising administering an agent which inhibits G-CSF or G-CSFR or inhibits the expression of G-CSF or G-CSFR and at least one other therapeutic agent such as an anti-inflammatory agent, immunosuppressive agent or other agent used in the treatment of uveitis.

In a particular embodiment, the present invention contemplates a method for the treatment of uveitis in a subject the method comprising administering to the subject an amount of an antibody or antigen-binding portion thereof effective to inhibit the activity of G-CSF or G-CSFR or G-CSF/G-CSFR interaction.

Yet another aspect provides a method for the treatment of uveitis in a subject the method comprising administering to the subject an amount of an antibody or antigen-binding portion thereof which is specific for hG-CSFR.

The present invention further contemplates the use of an agent which inhibits the activity of G-CSF or G-CSFR, or which inhibits the expression of G-CSF or G-CSFR in the manufacture of a medicament in the treatment of uveitis in a subject.

The present invention also provides the use of an agent which inhibits the activity of G-CSF or G-CSFR or which inhibits expression of a gene encoding G-CSF or G-CSFR, wherein the agent is selected from the group consisting of an antibody specific for G-CSF or G-CSFR; a soluble G-CSFR or a G-CSF-binding portion thereof; a 20 to 30 nucleotide sense or antisense molecule targeted to a nucleic acid molecule encoding G-CSF, the nucleic acid molecule comprising the sequence set forth in SEQ ID NO:3; and/or a 20 to 30 nucleotide sense or antisense molecule targeted to a nucleic acid molecule encoding a G-CSFR, the nucleic acid molecule comprising the sequence set forth in SEQ ID NO:7, in the manufacture of a medicament for the treatment of uveitis in a subject.

Still a further aspect contemplates the use of an agent which inhibits G-CSF or G-CSFR or which inhibits expression of G-CSF or G-CSFR wherein the agent is selected from the group consisting of:
  a. an antibody specific for G-CSF;
  b. an antibody specific for G-CSFR;
  c. a soluble G-CSFR or a G-CSF-binding portion thereof;
  d. a 20 to 30 nucleotide sense or antisense molecule targeted to a nucleic acid molecule encoding G-CSF, the nucleic acid molecule comprising the sequence set forth in SEQ ID NO:3; and
  e. a 20 to 30 nucleotide sense or antisense molecule targeted to a nucleic acid molecule encoding a G-CSFR, the nucleic acid molecule comprising the sequence set forth in SEQ ID NO:7 in the manufacture of a medicament for the treatment of uveitis in a subject.

In a particular embodiment, the present invention is directed to the use of an antibody to G-CSF or G-CSFR in the manufacture of a medicament for the treatment of uveitis in a subject.

An agent is also provided which inhibits the activity of G-CSF or G-CSFR or which inhibits expression of a gene encoding G-CSF or G-CSFR, wherein the agent is selected from the group consisting of an antibody specific for G-CSF or G-CSFR; a soluble G-CSFR or a G-CSF-binding portion thereof; a 20 to 30 nucleotide sense or antisense molecule targeted to a nucleic acid molecule encoding G-CSF, the nucleic acid molecule comprising the sequence set forth in SEQ ID NO:3; and a 20 to 30 nucleotide sense or antisense molecule targeted to a nucleic acid molecule encoding a G-CSFR, the nucleic acid molecule comprising the sequence set forth in SEQ ID NO:7 for use in the treatment of uveitis in a subject.

Animal models useful for testing inhibition of G-CSF or its receptor, or other approaches to antagonism of G-CSF-mediated signaling, include the experimental autoimmune uveitis (EAU) model.

In accordance with the present invention, suppression of G-CSF with a test antagonist had a significant impact on neutrophil number in the EAU model and reduced the level of disease in the model. As neutrophils are key mediators of ocular inflammation, the significant reduction in neutrophil numbers induced by the G-CSF antagonist in the EAU model indicates that the antagonism of G-CSF activity is a useful therapeutic approach.

The present invention is further described by the following non-limiting Examples.

EXAMPLE 1

Blocking G-CSF Inhibits Signs of Disease in EAU Model of Uveitis

Animals
C57B1/6 mice were used.
Disease Induction (Experimental Autoimmune Uveitis (EAU))

An emulsion was prepared by combining IRBP peptide (IRBP peptide is residues 1-20 of human interphotoreceptor retinal-binding protein) dissolved in PBS at 1.5 mg/ml with an equal volume of complete Freund's adjuvant (CFA) containing 2.5 mg/ml heat-killed *Mycobacterium tuberculosis*.

Disease was induced in mice by injection of a total of 200 μl emulsion s.c. into each flank of the mouse and into the base of the tail. Mice were also injected i.p. with 0.5 ml Pertussis solution (1 μg/ml Pertussis toxin in PBS+2% normal mouse serum). Each mouse therefore received 150 μg IRBP, 250 μg *M.tb*. and 0.5 μg Pertussis toxin.

Ab Blockade Studies

For studies into the blockade of G-CSF by monoclonal antibody treatment the following were used: anti-G-CSF mAb (clone 67604, purchased from R&D Systems) or isotype control mAb (clone GL113, rat IgG1). Mice were injected i.p. with 0.25 mg mAb on day 8 and then on every second day up to day 20.

Disease Assessment

Disease was assessed in mice by histological examination of mouse eyes after 21 days post-immunisation. Histological scoring of sections was performed blinded to the treatment groups and was based on the system of Caspi et al., *J Immunol*, 140(5):1490-5, 1988 and Shao et al., *J Immunol*, 175: 1851-7, 2005. Briefly, sections of each eye were scored from 0 (no disease) to 6 (severe disease) on histological features and number of lesions such as retinal folds, retinal detachment, loss of retina, vasculitis, infiltration into the vitreous or aqueous humor and inflammation of the ciliary body. Slides were scored in a blinded fashion.

Peripheral Blood Cell Analysis

Peripheral blood leucocyte numbers and differential WBC counts were determined on an Advia 120 automatic cell analyser. Blood was evaluated at 0, 7, 11, 15 and 21 days post immunization with IRBP.

ELISA for G-CSF

G-CSF levels in mouse sera were determined by sandwich ELISA using rat anti-G-CSF monoclonal Ab (clone 67604, R&D Systems) as capture Ab and biotinylated rabbit anti-G-CSF polyclonal Ab (R&D Systems) as detection antibody. Recombinant murine G-CSF (Peprotech) was used as standard.

Cytokine and Chemokine Levels

Vitreous and aqueous humor samples and serum were evaluated for cytokine and chemokine levels using the Bio-Plex mouse cytokine 23-plex panel (Bio-Rad Laboratories, Hercules, Calif., USA) according to the manufacturer's instructions. Humor samples were tested 1:3 diluted and serum samples were tested 1:4 diluted, in a test volume of 30 and 40 µl respectively. The assay was read on a Bio-Plex 200 instrument and analyzed using Bio-Plex Manager V5.0 software (Bio-Rad Laboratories, Hercules, Calif., USA).

ELISA for MPO

Myeloperoxidase (MPO) levels were quantitated using the Hbt mouse MPO ELISA test kit (cat. no. HK210) according to the manufacturer's instructions. Briefly, eyes were homogenized in sample buffer and levels were determined by plating onto antibody bound plates and detecting with anti-MPO bound to biotin. Mouse MPO was used as a standard.

Statistical Analysis

Analysis of differences between sample groups was performed using a Student's T test. Data shown is mean±SEM unless otherwise stated.

Results

Peripheral Blood Leucocytes are Elevated in EAU

After EAU induction, whole blood was taken and peripheral blood cell analysis performed (FIG. 1). White blood cells were increased dramatically at day 7, rising to approximately five fold higher than baseline. Levels remained elevated through days 11 to 21 although at lower levels. The increase in total leucocyte count was contributed to at day 7 and 11 by an increase in both neutrophils and lymphocytes, however the elevation at later time points (days 15 and 21) was due to significantly increased levels of neutrophils. Populations of neutrophils were increased approximately 35 fold above baseline levels at day 7, then 20 fold, and 10 fold at days 11, 15 and 21 respectively, whereas the increase in lymphocyte numbers was more modest with a 2.5 fold increase at day 7.

G-CSF Levels are Elevated in EAU and Correlate with Increases in Neutrophils

Figure 2:
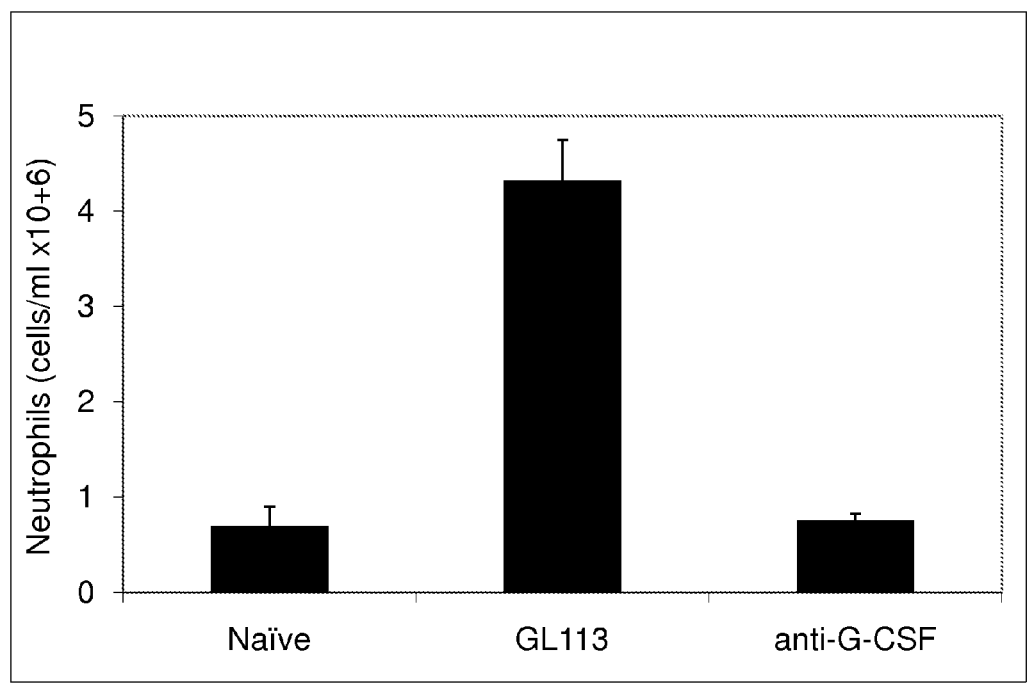
FIG. 2 is a graphical representation showing neutrophil levels in the blood in naïve mice and at day 21 after disease induction in mice where EAU was induced and then treated from days 8-20 every second day with either isotype control or anti-G-CSF Ab. n=10.

Serum levels of G-CSF were determined throughout the course of EAU by ELISA. Serum G-CSF rose rapidly and correlated with the increased numbers of neutrophils within the blood of mice during EAU (FIG. 2). G-CSF levels in WT untreated mice are normally undetectable, G-CSF levels rose significantly by day 7 and remained high throughout the course of disease.

Peripheral Levels of Th17 Type Cytokines Rise in EAU

Figure 3:
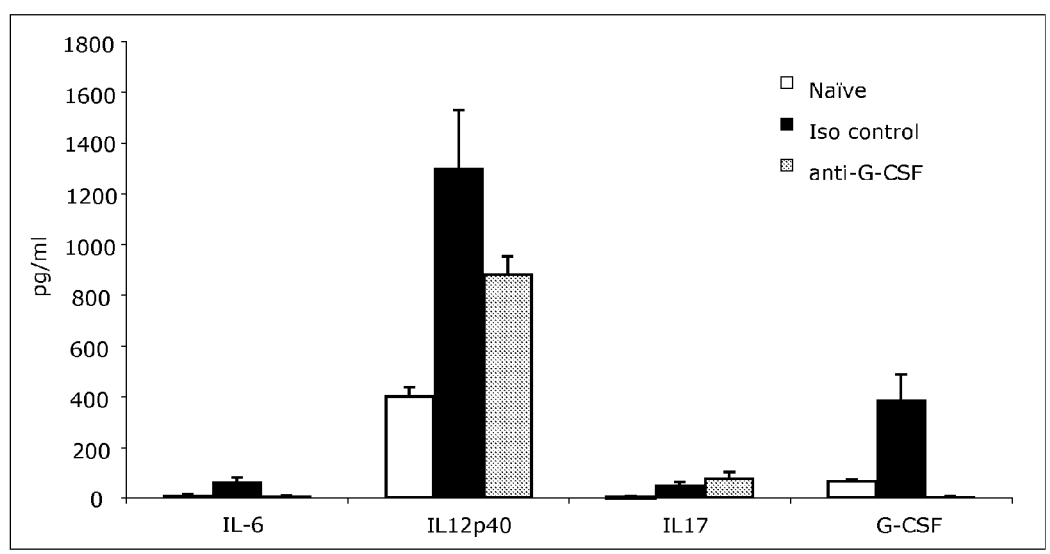
FIG. 3 is a graphical representation showing neutrophil levels in the blood in naïve mice and at day 21 after disease induction in mice where EAU was induced and then treated from days 8-20 every second day with either isotype control or anti-G-CSF Ab. n=3, *p<0.05.

Levels of cytokines in the serum of mice were measured after EAU induction. Rises in IL-6, IL-17 and the p40 subunit of IL-12 were observed (FIG. 3). Interestingly, small increases in the p70 subunit of IL-12, from a baseline 4.9±1.1 pg/ml increasing to 21.4±0.7 pg/ml at day 21. This was much smaller than the increases in IL-12p40 rising from a baseline of 403±34 pg/ml increasing to 1020±340 pg/ml at day 21. Thus the overall increases in IL-12p40 is not due to increases of this magnitude of IL-12. Another cytokine which also uses IL-12p70 is IL-23. These cytokines are all important in neutrophil biology.

Neutrophils Infiltrate the Eye in EAU

Myeloperoxidase (MPO) levels in the eye were determined by sandwich ELISA. MPO can be used as a quantifiable surrogate marker for neutrophil infiltration into the eye. Eye homogenates were found to have increasing levels of MPO during the course of EAU, peaking at maximal levels at day 21 (FIG. 4) correlating with histological features of disease. Neutrophils could also be seen in some lesions within the eye.

G-CSF and Th17 Type Cytokines are Elevated in the Eye in EAU

Eye fluid was taken by aspiration with needle and examined for production of cytokines. Increases in IL-6, IL-12p40 (but not IL-12p70) were observed which matched the increased seen in Th17 cytokines in the serum of EAU mice (FIG. 5).

G-CSF Antagonism Reduced the Severity and Incidence of EAU

Mice were treated with anti-G-CSF or isotype control from day 8 to day 20 after disease induction and were analysed at day 21. Eyes were taken for histology and blood was taken for serum analysis of cytokine levels and for determination of leucocyte populations. Treatment of mice with anti-G-CSF significantly reduced the overall severity of disease from 2.7±0.7 (WT mice) to 1.4±0.6 (anti-G-CSF treatment) (FIG. 6). Strikingly, most of the eyes examined in the anti-G-CSF treatment group had scores of only 0 or 1 indicating either no disease (score 0) or only minor infiltration into the vitreous humor with no retinal folds or obvious damage (score 1).

Anti-G-CSF Treatment Reduces Peripheral Neutrophils Levels in EAU to Levels of Naïve Untreated Mice Blood of mice treated with anti-G-CSF after EAU induction was analysed for neutrophil content. Neutrophils rise rapidly and remain elevated throughout EAU, however treatment with anti-G-CSF reduced these levels to that of naïve mice (FIG. 7). There was no significant difference between naïve mice ($0.7±0.2×10^6$ cells/ml) and EAU mice treated with anti-G-CSF ($0.8±0.1×10^6$ cells/ml) (p=0.43).

IL-6 and IL-12p40 Levels are Reduced After Anti-G-CSF Treatment in EAU

Serum cytokine levels were measured of mice treated with anti-G-CSF after EAU induction. IL-6 was reduced to levels similar to those of naïve mice. IL-12p40 was also reduced although remained above that of naïve mice and IL-17 was unchanged. G-CSF was undetectable in mice treated with anti-G-CSF as expected. The reduction in not only G-CSF but some of the Th17 type cytokines may also contribute to the reduced neutrophil levels after anti-G-CSF treatment.

Discussion

The levels of neutrophils and G-CSF rise in the peripheral blood rapidly in EAU, rising rapidly by day 7 and remaining elevated throughout the course of disease induction to day 21. An increase in neutrophil levels was also observed in the eye. IL-6, IL-12p40 and IL-17 were also increased in the serum throughout disease and in the eye at day 21. These cytokines are important in neutrophil production and function and may contribute together with the effects of G-CSF to the increased neutrophil levels seen in the peripheral blood and within the eye. Depletion of G-CSF by treatment with a neutralizing antibody from day 8 to day 21 decreased the severity of EAU disease. Interestingly, depletion of G-CSF reduces neutrophils in the peripheral blood to naïve levels. Neutrophils are important for control of infection and low levels of neutrophils can lead to increased infection with opportunistic micro-organisms. G-CSF depletion in EAU did not reduce neutrophil levels to that below normal mice and therefore should not compromise neutrophil responses to infectious agents.

EXAMPLE 2

Inhibition of G-CSF Mediated Proliferation in hG-CSF Receptor Expressing BA/F3 Cells by Various G-CSF Antagonists BaF3 cells stably transfected with hG-CSFR as described by Layton et al., *J. Biol. Chem.* 272:29735-29741, 1997 were cultured in 96 well plates at 20,000 cells/well in DMEM media with 5% v/v FBS and 0.5 ng/ml rh or mGCSF (R&D Systems Cat #214-CS and Cat #414-CS respectively). G-CSF antagonists (R&D Systems MAB414, anti-hG-CSFR mAb711 and hG-CSFR-Fc) were added at threefold titrating doses starting from 1 µM and cell proliferation measured by MTS reduction (Cory et al., *Cancer Commun.* 3:207-12, 1991; Riss and Moravec, *Mol. Cell Biol.* 3(1):184a, 1993) after 48 hours culture.

A. Inhibition by Anti-G-CSF Antibody:
Anti-G-CSF (MAB414) was able to inhibit mG-CSF proliferation with an $IC_{50}$ of 10 pM.

B. Inhibition by Anti-hG-CSFR Antibody:
A murine monoclonal antibody against the hG-CSF Receptor, mAb711, (Layton et al., supra 1997) and its humanized derivative were able to inhibit mG-CSF proliferation with $IC_{50}$'s of 1.1 nM and 1.5 nM respectively.
A chimeric antibody comprising the heavy and light chain variable regions of mAb711 and human IgG1 heavy and light chain constant regions inhibited G-CSF activity with a similar $IC_{50}$ to the murine monoclonal antibody mAb711.

C. Inhibition by Soluble hG-CSFR-Fc Protein:
A soluble G-CSFR-Fc protein (Honjo et al., *Acta Cryst* F61:788-790, 2005) was able to inhibit mG-CSF proliferation with an $IC_{50}$ of 22 pM.

These results demonstrate that the biological activity of G-CSF is inhibited by a variety of antagonists, including but not limited to, antibodies to G-CSF, antibodies to G-CSFR, and soluble G-CSF receptors.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Banerjee et al., *Invest Ophthalmol Vis. Sci.* 48(5):2203-2207, 2007
Bialek et al., *Infection* 26(6):375-8, 1998
Bird, *Science* 242:423, 1988
Boven et al., *Clin Exp Immunol* 122(2):257-63, 2000
Brennan et al., *Science* 229:81, 1985
Bungart et al., *British Journal of Haematology* 22:1156, 1990
Carter et al., *Bio/Technology* 10:163-167, 1992
Caspi et al., *J Immunol,* 140(5):1490-5, 1988
Clackson et al., *Nature* 352:624-628, 1991
Colotta et a.l, *Blood* 80:2012-2020, 1992
Cory et al., *Cancer Commun.* 3:207-12, 1991
Dagia et al., *Nat Med* 12(10):1185-90, 2006
de Haan et al., *Blood* 86:2986-2992, 1995
Demetri et al., *Blood* 78:2791-2808, 1991
Dibbert et al., *Proc Natl Acad Sci USA* 96(23):13330-5, 1999
Duhrsen et al., *Blood,* 72(6):2074-81, 1988
Esmaeli et al., *Cornea,* 21(6):621-2, 2002
Eyles et al., *Nat Clin Pract Rheumatol,* 2(9):500-510, 2006
Eyles et al., *Blood* 112(13):5193-201, 2008
Frank et al., *BMC Neurosci* 10:49, 2009
Fraunfelder and Harrison, *Cornea,* 26(3):368-9, 2007
Fuchsjäger-Mayrl et al., *Invest Ophthalmol Vis. Sci.,* 43(5):1520-4, 2002
Geng et al., *Molecular Immunology* 44:5121-529, 2007
Gericke et al., *Journal of Leukocyte Biology* 57:455-461, 1995
Goto et al., *Nippon Ganka Gakkai Zasshi,* 98(10):1019-26, 1994
Graff et al., *Journal of pharmacological and toxicological methods,* 39(3):169-78, 1998
Gritz et al., *Current Eye Research,* 10(10):927-31, 1991
Hashida et al., *Invest Ophthalmol Vis. Sci.,* 46(11):4224-34, 2005
Hong et al., *Invest Ophthalmol Vis. Sci.,* 42(12):2795-803, 2001
Honjo et al., *Acta Crystallogr Sect F Struct Biol Cryst Commun.* 61(Pt 8):788-790, 2005
Huston et al., *Proc. Natl. Acad. Sci. USA* 85:5879, 1988
Imrie and Dick, *Current opinion in ophthalmology,* 18(6):481-6, 2007
Jacob et al., *Blood* 92:353-361, 1998
Jones et al., *Nature* 321:522-525, 1986
Kabat et al in *Sequences of Proteins of Immunological Interest,* 5th Ed., US Department of Health and Human Services, PHS, NIH, NIH Publication No. 91-3242, 1991
Kawakami et al., *Arch Dermatol,* 140(5):570-4, 2004
Kohler and Milstein, *Nature* 256:495-499, 1975
Kortt et al., *Protein Engineering* 10:423, 1997
Langrish et al., *J Exp Med* 201(2):233-40, 2005
Larrick et al., *Bio/Technology* 7:934, 1989
Lawlor et al., *Proc Natl Acad Sci USA,* 101(31):11398-403, 2004
Layton et al., *J. Biol. Chem.* 272:29735-29741, 1997
Liu et al., *Proc. Natl. Acad. Sci. USA* 84:3439, 1987
Lord et al., *Proc. Natl. Acad. Sci. USA* 86:9499-9503, 1989
Marks et al., *J. Mol. Biol.* 222:581-597, 1991
Metcalf, *International Journal of Cancer* 25:225, 1980
Morimoto et al., *Journal of Biochemical and Biophysical Methods* 24:107-117,1992
Morrison et al., *Proc. Nat. Acad. Sci.* 81:6851, 1984
Nicola et al., *Journal of Biological Chemistry* 258:9017, 1983
Nicola et al., *Nature* 314:625, 1985
Padlan et al., *Mol. Immunol.* 28:489-498, 1991
Parkkali et al., *Bone Marrow Transplant,* 17(3):433-4, 1996
Pedersen et al., *J. Mol. Biol.* 235:959-973, 1994
Presta, *Curr. Op. Struct. Biol.* 2:593-596, 1992
Reichmann et al., *Nature* 332:323-329, 1988
Rex et al., *Transfusion* 35:605-611, 1995
Riss and Moravec, *Mol. Cell Biol.* 3(1):184a, 1993
Roberts et al., *Blood* 89:2736-2744, 1997
Roberts, *GGRF,* 23(1):33-41, 2005
Sambrook, Fritsch & Maniatis, *Molecular Cloning: A Laboratory Manual,* Second Edition (1989) Cold Spring Harbor Laboratory Press, Cold Spring Harbor, N.Y.; DNA Cloning: *A Practical Approach,* Volumes I and II, D. N. Glover ed. 1985 and Ausubel et al. (eds.), *Current Protocols in Molecular Biology,* John Wiley & Sons, Inc., 1994
Sheridan et al., *Lancet,* 339(8794):640-4, 1992
Shao et al., *J Immunol,* 175:1851-7, 2005
Souza et al., *Science* 232:61, 1986
Summerton and Weller, *Antisense and Nucleic Acid Drug Development* 7:187-195, 1997
Takahama et al., *J Dermatol,* 21(8):546-52, 1994
Tsuchiyama et al., *Ann Hematol,* 79(5):269-71, 2000
Ward et al., *Nature* 334:544, 1989
Welte et al., *Blood* 88:1907-1929, 1996
Winter & Harris, *TIPS* 14:139, 1993; Carter et al., *Proc. Nat. Acad. Sci.* 89:4285 1992
Xu et al., *British Journal of Haematology* 93:558-568, 1996
Yamada et al., *Journal of free radicals in biology & medicine,* 2(2):111-7, 1986
Yong et al., *European Journal of Haematology* 49:251-259, 1992
Yong, *British Journal of Haematology* 94:40-47, 1996

The invention claimed is:

1. A method for treating uveitis in a subject, said method comprising administering to said subject an effective amount of a Granulocyte-Colony Stimulating Factor- (G-CSF-) or Granulocyte-Colony Stimulating Factor Receptor- (G-CSFR-) inhibiting agent selected from the group consisting of an antibody specific for G-CSF and an antibody specific for G-CSFR; for a time and under conditions sufficient to ameliorate the symptoms of uveitis.

2. The method of claim 1, wherein the G-CSF or G-CSFR antibody is an antigen binding fragment specific for G-CSF or G-CSFR.

3. The method of claim 1 wherein the subject is a human.

4. The method of claim 3 wherein the antibody is specific for human G-CSFR (hG-CSFR).

5. The method of claim 1 further comprising the administration of an agent used in the treatment of uveitis.

6. The method of claim 1 or 4 wherein the antibody specific for G-CSF or G-CSFR is a monoclonal antibody.

7. The method of claim 6 wherein the antibody is a chimeric, human or humanized antibody.

8. The method of claim 6 wherein the antibody is a human antibody.

* * * * *